United States Patent [19]

Husa et al.

[11] Patent Number: 5,304,644

[45] Date of Patent: Apr. 19, 1994

[54] 1-,2-,3-,4-,5-,6-,7-,8- AND/OR 9 SUBSTITUTED DIBENZOXAZEPINE COMPOUNDS, PHARMACEUTICAL COMPOSITIONS AND METHODS FOR TREATING PAIN

[75] Inventors: Robert K. Husa, Vernon Hills; Michael F. Rafferty, Buffalo Grove; Timothy J. Hagen, Glenview; E. Ann Hallinan, Evanston, all of Ill.

[73] Assignee: G. D. Searle & Co., Chicago, Ill.

[21] Appl. No.: 869,563

[22] Filed: Apr. 15, 1992

[51] Int. Cl.$^5$ .................................... C07D 267/20
[52] U.S. Cl. .................................... 540/547
[58] Field of Search .................... 540/547; 514/211

[56] References Cited

U.S. PATENT DOCUMENTS

| | | | |
|---|---|---|---|
| 3,534,019 | 10/1970 | Coyne et al. | 540/547 |
| 3,624,104 | 11/1971 | Cusic et al. | 540/547 |
| 3,917,649 | 11/1975 | Mueller | 540/547 |
| 3,989,719 | 11/1976 | Mueller | 540/547 |
| 3,992,375 | 11/1976 | Mueller | 540/547 |
| 4,045,442 | 8/1977 | Mueller | 540/547 |
| 4,125,532 | 11/1978 | Mueller | 540/547 |
| 4,170,593 | 10/1979 | Mueller | 540/547 |
| 4,559,336 | 12/1985 | Mueller | 540/547 |
| 4,559,337 | 12/1985 | Mueller | 540/547 |
| 4,614,617 | 9/1986 | Mueller | 540/547 |
| 4,704,386 | 11/1987 | Mueller | 540/547 |

FOREIGN PATENT DOCUMENTS

| | | |
|---|---|---|
| 0012385 | 6/1980 | European Pat. Off. . |
| 0193822 | 9/1986 | European Pat. Off. . |
| 0218077 | 4/1987 | European Pat. Off. . |
| 6700603 | 7/1967 | Netherlands . |
| 1170322 | 11/1969 | United Kingdom . |
| 1331892 | 9/1973 | United Kingdom . |
| 1522003 | 8/1978 | United Kingdom . |

OTHER PUBLICATIONS

Drower, et al., "The Antiociceptive Effects of Prostaglandin Antagonists in the Rat," European Journal of Pharmacology, 133, 249–256 (1987).

J. H. Sanner, "Dibenzoxazepine Hydrazides as Prostaglandin Antagonists," Intra-Science Chem. Rept., vol. 6, No. 1, 1–9 (1972).

K. Nagarajan, et al., "Synthesis of 10,11-Dihydrodibenz[b,f][1,4]oxazepine Derivatives as Potential Anticonvulsants & Psychotropic Agents," *Indian Journal of Chemistry*, vol. 24B, 840–844 (1985).

D. E. MacIntyre, et al., "Antagonism of Human Platelet Responses to Stimulatory and Inhibitory Prostaglandins," *Prog. Lipid. Res.* 20 (1–4), 453–9 (1981).

(List continued on next page.)

*Primary Examiner*—Mukund J. Shah
*Assistant Examiner*—Philip Datlow
*Attorney, Agent, or Firm*—Roberta L. Hastreiter; Roger A. Williams

[57] ABSTRACT

The present invention provides substituted dibenzoxazepine compounds of Formula I:

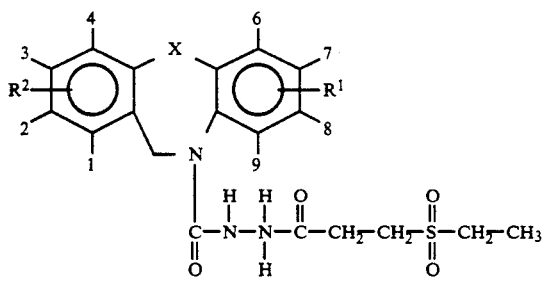

which are useful as analgesic agents for the treatment of pain, pharmaceutical compositions comprising a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

3 Claims, No Drawings

OTHER PUBLICATIONS

R. Gimet, et al., "Quantitative Determination of Polymorphic Forms in a Formulation Matrix Using the Near Infra-Red Reflectance Analysis Technique," *J. Pharmaceutical & Biomedical Analysis*, vol. 5, No. 3, 205–211 (1987).

J. H. Sanner, et al., "Structure-Activity Relationships of some Dibenzoxazepine Derivatives as Prostaglandin Antagonists," *Advances in the Biosciences*, 9, 139–148 (1972).

A. Rakovska, et al., "Antagonistic Effect of SC-19220 on the Responses of Guinea-Pig Gastric Muscles to Prostaglandins E1, E2 and F2," *Arch Int. Pharmacodyn.*, 268, 59–69 (1984).

W. E. Coyne, et al., "Anticonvulsant Semicarbazides," *J. Med. Chem.*, 11(6), 1158–1160 (1968).

K. Gyires, et al., "The Use of the Writhing Test in Mice for Screening Different Types of Analgesics," *Arch. Int. Pharmacodyn.*, 267, 131–140 (1984).

A. Bennett, et al., "Antagonism of Prostanoid-Induced Contractions of Rat Gastric Fundus Muscle by SC-19220, Sodium Meclofenamate, Indomethacin or Trimethoquinol," *Br. J. Pharmac.*, 71, 169–175 (1980).

C. A. Maggi, et al., "The Effect of SC-19220, a Prostaglandin Antagonist, on the Micturition Reflex in Rats," *European Journal of Pharmacology*, 152, 273–279 (1988).

George, et al., "Antagonism of Alcohol Hypnosis by Blockade of Prostaglandin Synthesis and Activity: Genotype and Time Course Effects," *Pharmacology Biochemistry & Behavior*, vol. 19, 131–136 (1983).

S. Nakajyo, et al., "Inhibitory Effect of Bassianolide, A Cyclodepsipeptide, on Drug-Induced Contractions of Isolates Smooth Muscle Preparations," Japan J. Pharmacol., 32, 55–64 (1982).

A. Gomes, et al., "Pharmacodynamics Venom of the Centipede *Scolopendra* subspinipes dehaani," *Indian Journal of Experimental Biology*, vol. 20, 615–618 (1982).

1-,2-,3-,4-,5-,6-,7-,8- AND/OR 9 SUBSTITUTED DIBENZOXAZEPINE COMPOUNDS, PHARMACEUTICAL COMPOSITIONS AND METHODS FOR TREATING PAIN

BACKGROUND OF THE INVENTION (1) Field of the Invention

The present invention generally relates to compounds having pharmacological activity which are useful as pharmaceutical agents and, more particularly, as analgesic agents for the treatment of pain, to pharmaceutical compositions containing one or more of these compounds, and to methods of treatment employing these compounds. More particularly, the present invention concerns substituted dibenzoxazepine compounds, pharmaceutical compositions containing one or more of these compounds in combination with a pharmaceutically-acceptable carrier, and medical methods of treating pain employing these compounds.

Analgesic compounds are agents which alleviate pain without causing a loss of consciousness and, thus, which are useful for treating pain and, often, for reducing inflammation.

The major classes of analgesic compounds include narcotic analgesics, or opiates, compounds which alleviate pain and induce sleep, and analgesic-antipyretic compounds, compounds which alleviate pain and reduce fever, such as salicylates.

Although the efficacy of opiates in relieving pain is well established, the associated addiction liability of opiates is a distinct disadvantage of these compounds.

While salicylate and salicylate-like agents (non-steroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

The compounds of the present invention are neither opiates nor salicylates, and represent another class of compounds which are useful as analgesic agents.

(2) Description of the Related Art

U.S. Pat. Nos. 4,559,336 and 4,614,617 (a continuation-in-part of U.S. Pat. No. 4,559,336) disclose 8-chlorodibenz[b,f] [1,4]-oxazepine-10(11 H)-carboxylic acid, 2-(sulfinyl- and sulfonyl-containing acyl)hydrazides, and intermediates thereof.

U.S. Pat. No. 3,534,019 discloses hydrazides of dibenzoxazepine-, dibenzothiazepine- and dibenzodiazepine-carboxylic acids.

U.S. Pat. No. 3,624,104 discloses aralkanoyl derivatives of dibenzoxazepine-N-carboxylic acid hydrazide compounds.

U.S. Pat. No. 3,989,719 discloses N,N'-diacyl hydrazines.

U.S. Pat. Nos. 3,917,649 and 3,992,375 (a divisional of U.S. Pat. No. 3,917,649) disclose dibenzoxazepine N-carboxylic acid hydrazine compounds.

U.S. Pat. Nos. 4,045,442, 4,125,532 (a divisional of U.S. Pat. No. 4,045,442) and 4,170,593 (a divisional of U.S. Pat. No. 4,125,532) disclose 1-(substituted amino-)alkanoyl-2-(dibenzoxazepine-10-carbonyl)hydrazine compounds.

U.S. Pat. No. 4,559,337 discloses 8-chlorodibenz-[b,f] [1,4]-oxazepine-10(11 H)-carboxylic acid, 2-(alkoxy-containing acyl)hydrazide compounds.

GB 1 522 003 discloses 1-acyl-2-(8-chloro-10,11-dihydrodibenz [b,f] [1,4]oxazepine-10-carbonyl)hydrazine compounds.

GB 1 331 892 discloses derivatives of dibenzoxazepine N-carboxylic acid hydrazides.

European Patent Application Publication No. 0 012 385 discloses dibenz[b,f] [1,4]oxazepine derivatives.

German Patent Application Publication No. 1,170,322 discloses 10-substituted dibenz[b,f][1,4]oxazepine-11(10 H)-ones.

European Patent Application Publication No. 0 193 822 discloses 8-chlorodibenz[b,f][1,4]-oxazepine-10(11 H)-carboxylic acid, 2-(thio-, sulfinyl- and sulfonyl-containing acyl)hydrazide compounds.

European Patent Application Publication No. 0 218 077 discloses 8-chlorodibenz[b,f][1,4]oxazepine-10(11 H)-carboxylic acid, 2-[(substituted phenylsulfinyl)alkanoyl]hydrazide compounds and 8-chlorodibenz [b,f][1,4]oxazepine-10(11 H)-carboxylic acid, 2-[(substituted phenylsulfonyl)alkanoyl]hydrazide compounds, and intermediates used in the preparation of these compounds.

Netherlands Patent No. 67,00603 discloses substituted dibenz[b,f][1,4]oxazepine-11(10H)-one compounds.

Drower et al., "The Antiociceptive Effects of Prostaglandin Antagonists in the Rat," *European Journal of Pharmacology*, 133, 249–256 (1987), disclose the study of the antinociceptive properties of two competitive antagonists of prostaglandins of the E series, 8-chlorodibenz[b,f][1,4]-oxazepine-10(11 H)-carboxylic acid, 2-acetylhydrazide and 8-chlorodibenz[b,f][1,4]-oxazepine-10(11 H)-carboxylic acid, 2-(5-chloro-1-oxopentyl)-hydrazide.

J. H. Sanner, "Dibenzoxazepine Hydrazides as Prostaglandin Antagonists," *Intra-Science Chem. Rept.*, 6(1), 1–9 (1972), describes experiments performed with two dibenzoxazepine derivatives designated SC-18637 and SC-19220, and shown below, and found that SC-18637 and SC-19220 inhibit the stimulant actions of prostaglandins on isolated smooth muscle preparations.

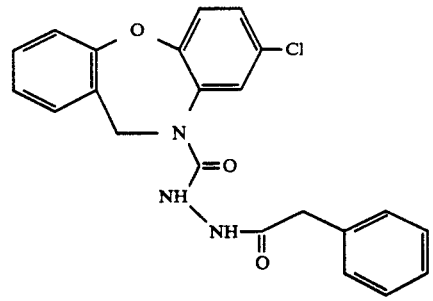

SC-18637

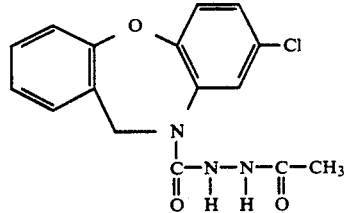

SC-19220

K. Nagarajan et al., "Synthesis of 10,11-Dihydrodibenz [b,f][1,4]oxazepine Derivatives as Potential Anticonvulsants & Psychotropic Agents," *Indian Journal of*

*Chemistry*, 24B, 840-844 (1985), disclose the synthesis of acyl, carbamoyl and thiocarbamoyl derivatives of 10,11-dihydrodibenz [b,f][1,4]oxazepine, most of which have either a nitro or an amino group at position-2, as analogues of carbamazepine, and the evaluation of these derivatives as anticonvulsants associated with neuroleptic activity.

Other art which relates to the present invention includes that which is discussed below.

D.E. MacIntyre et al., "Antagonism of Human Platelet Responses to Stimulatory and Inhibitory Prostaglandins," *Prog. Lipid. Res.*, 20(1-4), 453-9 (1981), disclose on Page 454, Lines 11-12, Page 458, Lines 43-44, and in Table 1, two dibenzoxazepine compounds designated SC-19220 and SC-25191, and shown above and below, respectively, which were employed in an investigation of the effects of prostaglandin antagonists on platelet responses to stimulatory and inhibitory prostaglandins.

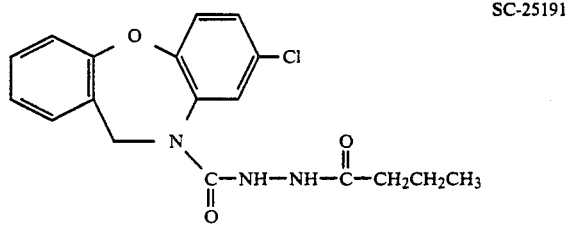

SC-25191

R. Gimet et al., "Quantitative Determination of Polymorphic Forms in a Formulation Matrix Using the Near Infra-Red Reflectance Analysis Technique," *J. Pharmaceutical & Biomedical Analysis*, 5(3), 205-211 (1987), disclose an analytical method for the determination of the polymorphic transformation of an active ingredient in a solid dosage form matrix, and discuss a compound designated SC-25469, and shown below, at Page 206, Lines 16-23.

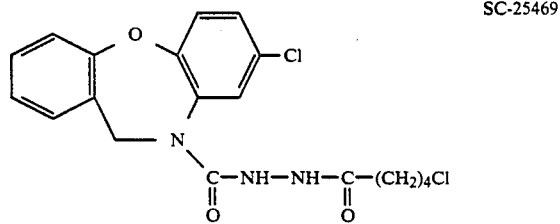

SC-25469

J.H. Sanner et al., "Structure-Activity Relationships of some Dibenzoxazepine Derivatives as Prostaglandin Antagonists," *Advances in the Biosciences*, 9, 139-148 (1972), disclose tests for prostaglandin antagonism on isolated guinea-pig ileum and rat stomach fundus strips with the n-butanoyl, i-butanoyl and n-hexanoyl analogs of SC-19220 and, on Page 140, Lines 11-18, show the chemical structures of the compounds used in the study.

A. Rakovska et al., "Antagonistic Effect of SC-19220 on the Responses of Guinea-Pig Gastric Muscles to Prostaglandins $E_1$, $E_2$ and $F_2$," *Arch. int. Pharmacodyn*, 268, 59-69 (1984), disclose a study of the contractile responses of guinea-pig gastric muscles to SC-19220, and the prostaglandin-blocking activity and specificity of SC-19220 on these muscles.

W. E. Coyne et al., "Anticonvulsant Semicarbazides," *J. Med. Chem.*, 11(6), 1158-1160 1968), disclose the investigation of the structure-activity relationship of the anticonvulsant activity of a series of semicarbazides which was synthesized from various tricyclic amines (see Table 1, Page 1160).

K. Gyires et al., "The Use of the Writhing Test in Mice for Screening Different Types of Analgesics," *Arch. int. Pharmacodyn*, 267, 131-140 (1984), describe a comparison of the analgesic potency of some prostaglandin synthesis inhibitors and morphine using the writhing test. SC-19220 is discussed on Page 133, Lines 10 and 14-16, in Table II (Page 134), and on Page 135, Lines 16-25, and Page 137, Lines 34-38.

A. Bennett et al., "Antagonism of Prostanoid-Induced Contractions of Rat Gastric Fundus Muscle by SC-19220, Sodium Meclofenamate, Indomethacin or Trimethoquinol," *Br. J. Pharmac*, 71, 169-175 (1980), disclose the study of the effects of several compounds, including SC-19220, on contractions of the rat stomach longitudinal muscle to several prostanoids. SC-19220 is discussed on Page 175, Paragraph 1, Page 170, Paragraph 4, in Table 1 and FIG. 2, on Page 172, Paragraph 2, and on Page 174, Paragraphs 1 and 2.

C.A. Maggi et al., "The Effect of SC-19220, a Prostaglandin Antagonist, on the Micturition Reflex in Rats," *European Journal of Pharmacology*, 152, 273-279 (1988), disclose a study in which SC-19220 is said to have increased the bladder capacity and reduced the voiding efficiency of micturition of urethane-anesthetized rats.

George et al., "Antagonism of Alcohol Hypnosis by Blockade of Prostaglandin Synthesis and Activity: Genotype and Time Course Effects," *Pharmacology Biochemistry & Behavior*, 19, 131-136 (1983), disclose a study of genetic and time-course factors of the effect of the antagonism of alcohol-induced behaviors of mice which have been pretreated with prostaglandin synthetase inhibitors and the effect of SC-19220 on ethanol sleep time.

S. Nakajyo et al., "Inhibitory Effect of Bassianolide, A Cyclodepsipeptide, on Drug-Induced Contractions of Isolated Smooth Muscle Preparations,"*Japan. J. Pharmacol.*, 32, 55-64 (1982), disclose a study of the effect of bassianolide on the contractile responses induced by various types of neurotransmitters and autacoids. SC-19220 was employed in this study and is discussed on Page 57, Paragraph 1, in FIGS. 2 and 3, in Table 1, and on Page 60, Paragraph 1, Page 62, Paragraph 3, and Page 63, Paragraph 2.

A. Gomes et al., "Pharmacodynamics of Venom of the Centipede *Scolopendra subspinipes dehaani*,"*Indian Journal of Experimental Biology*, 20, 615-618 (1982), disclose an investigation of the pharmacodynamic actions of the venom of the tropical centipede *S. subspinipes*. SC-19220 was employed in this study and is discussed on Page 615 (abstract), Page 616, Line 30, Page 617, Lines 13-18, in FIGS. 4 and 5, and on page 618, Lines 23-26.

Each of the documents described hereinabove discloses compounds which are structurally different from the compounds of the present invention. Thus, the compounds of the present invention are structurally distinct from that which has been described in the art.

Compounds of the present invention have been found to exhibit activity as prostaglandin $E_2$ antagonists.

SUMMARY OF THE INVENTION

The present invention provides compounds having a structure of Formula I:

Formula I

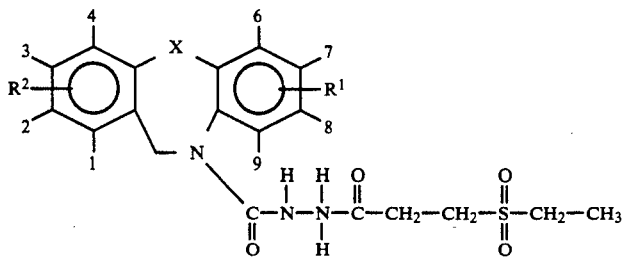

or a pharmaceutically-acceptable salt, ester or amide thereof, wherein:

X is oxygen, sulfur,

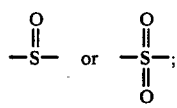

R¹ is hydrogen, hydroxy, alkyl, haloalkyl, alkoxy, carboxy, alkoxycarbonyl, amino, aminocarbonyl, alkylamino, dialkylamino, amido, halogen, cyano, nitro, trifluoromethyl, sulfonamide, phosphonate, urea or urethane; and R² is hydrogen or halogen;

with the proviso that R¹ is not chlorine at position 8 when X is oxygen and R² is hydrogen.

The present invention also provides pharmaceutical compositions which are pharmaceutically acceptable and which comprise a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

DETAILED DESCRIPTION OF THE INVENTION

(1) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The abbreviations "AcOH" and "HOAc" as used herein mean acetic acid.

The term "alkyl" as used herein means a saturated hydrocarbon radical having from one to ten carbon atoms, and within which includes from one to six carbon atoms, and further within which includes from one to three carbon atoms, which can be a straight or branched chain. Representative of such radicals are methyl, ethyl, propyl, isopropyl, butyl, sec-butyl, isobutyl, tert-butyl, pentyl and the like.

The term "alkylamino" as used herein means an amino group, as defined below, which has one of the hydrogen atoms replaced by an alkyl group, as defined above.

The term "alkoxy" as used herein means an alkyl radical, as defined above, having an oxygen atom attached thereto. Representative alkoxy groups include methoxy, ethoxy, propoxy, tert-butoxy and the like.

The term "alkoxycarbonyl" as used herein means an alkoxy group, as defined above, having a carbonyl group attached thereto, as defined below.

The abbreviation "AlMe₃" as used herein means trimethylaluminum.

The term "amino" as used herein means an —NH₂ group.

The term "aminocarbonyl" as used herein means a carbonyl group, as defined below, which has an amino group, as defined above, attached thereto.

The term "amido" as used herein means a

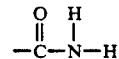

group.

The term "analgesia" as used herein means the reduction, or absence, of sensibility to pain, designating particularly the relief of pain without loss of consciousness.

The term "animal" as used herein includes mammals and nonmammals, and further includes humans and non-human mammals.

The term "aryl" as used herein means 5- and 6-membered single-ring aromatic radicals which may include from zero to four heteroatoms. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The abbreviation "Boc" as used herein means t-butyloxycarbonyl.

The abbreviation "Calc." as used herein means calculated.

The term "carbonyl" as used herein means a

group.

The term "carboxy" as used herein means a

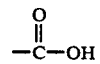

group.

The term "composition" as used herein means a product which results from the combining of more than one element or ingredient.

The term "cyano" as used herein means a —CN group.

The term "dialkylamino" as used herein means an amino group, as defined above, which has both of the hydrogen atoms replaced by an alkyl group, as defined above.

The abbreviation "DMAP" as used herein means 4-(dimethylamino)pyridine.

The abbreviation "DMF" as used herein means dimethylformamide.

The abbreviation "DSC" as used herein means Differential Scanning Calorimetry.

The phrase "$EC_{50}$ concentration" as used herein means that concentration of a compound or drug which is necessary to elicit a 50% maximal biological response and, thus, which is necessary to elicit a 50% reduction in the contractions of guinea pig ileum segments in a prostaglandin antagonism assay.

The phrase "$ED_{50}$ dose" as used herein means that dose of a compound or drug which produced a biological effect, such as producing analgesia, in 50% of the animals to which the compound or drug was administered.

The abbreviation "Et" as used herein means ethyl ($-CH_2CH_3$).

The abbreviation "EtOAc" as used herein means ethyl acetate.

The abbreviation "EtOH" as used herein means ethanol ($CH_3CH_2OH$).

The abbreviation "$Et_3N$" as used herein means triethylamine.

The term "halo" or "halogen" as used herein means chlorine (Cl), bromine (Br), fluorine (F) and/or iodine (I).

The term "haloalkyl" as used herein means an alkyl radical, as defined above, which has one or more hydrogen atoms replaced by a halogen atom, as defined above, including, but not limited to, fluoromethyl, 2-chloroethyl, trifluoromethyl, 2,2-dichloroethyl and the like.

The term "heteroatom" as used herein means an atom of any element other than carbon or hydrogen.

The abbreviation "$^1H$ NMR" as used herein means Proton Nuclear Magnetic Resonance.

The abbreviation "HPLC" as used herein means High Pressure Liquid Chromatography.

The term "hydroxy" as used herein means the group —OH.

The term "intragastrically" and/or the abbreviation "i.g." as used herein means that a compound or drug was administered into the stomach.

The abbreviation "i.p." as used herein means that a compound or drug was administered intraperitoneally.

The abbreviation "IR" as used herein means infrared, referring to an infrared spectrum.

The abbreviation "LAH" as used herein means lithium aluminum hydride.

The abbreviation "Me" as used herein means methyl ($-CH_3$).

The abbreviation "MeOH" as used herein means methanol ($CH_3OH$).

The abbreviation "mp" as used herein means melting point.

The abbreviation "MPLC" as used herein means Medium Pressure Liquid Chromatography.

The term "nitro" as used herein means an $-NO_2$ group.

The abbreviation "n-BuLi" as used herein means n-butyl lithium.

The abbreviation "NMR" as used herein means Nuclear Magnetic Resonance.

The abbreviation "n-Pr" as used herein means n-propyl.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmitate, stearate, laurate, benzoate, lactate, phosphate, tosylate, citrate, maleate, fumarate, succinate, tartrate, napsylate, clavulanate and the like salts, and alkali metal salts, such as sodium and potassium, and alkaline earth salts, such as calcium and magnesium.

The term "phosphonate" as used herein means a

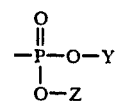

group, wherein Y and Z may be the same or different, and may be hydrogen, alkyl or aryl.

The abbreviation "p.o." as used herein means that a compound or drug was administered orally.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acetyl, pivaloyl, t-butyloxycarbonyl (Boc), carbonylbenzyloxy (Cbz), benzoyl and an L- or D-aminoacyl residue, which may itself be N-protected similarly.

The abbreviation "RaNi" as used herein means Raney nickel.

The abbreviation "s.c." as used herein means that a compound or drug was administered subcutaneously.

The term "sulfonyl" as used herein means an

group.

The term "sulfonamide" as used herein means an

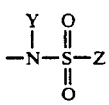

group, wherein Y is hydrogen, alkyl or aryl, and wherein Z is alkyl or aryl.

The abbreviation "t-Bu" as used herein means tert-butyl.

The abbreviation "TEA" as used herein means triethylamine.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The abbreviation "THF" as used herein means tetrahydrofuran.

The phrases "title compound," "title product" and "title material" as used herein mean that compound, product or material whose chemical name is given, and/or whose structure is shown, in the particular example, or subpart thereof, referred to. If no particular example, or subpart thereof, is referred to, it means that compound, product or material whose chemical name is given, and/or whose structure is shown, in the particular example, or subpart thereof, in which it appears.

The term "trifluoromethyl" as used herein means a —CF$_3$ group.

The term "urea" as defined herein means an

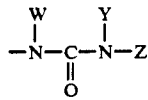

group, wherein each of W, Y and Z is the same or different, and may be hydrogen, alkyl or aryl.

The term "urethane" as used herein means an

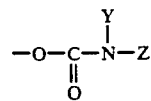

group, wherein Y and Z may be the same or different, and may be hydrogen, alkyl or aryl.

(2) Description of Invention

In one aspect, the present invention provides compounds comprising a structure of Formula I, as described above, and pharmaceutically-acceptable salts, esters and amides thereof.

The compounds of the present invention comprise a class of substituted dibenzoxazepine compounds in which the 1, 2, 3, 4, 5, 6, 7, 8 and/or 9-position is substituted. Compounds within the present invention have been shown to exhibit activity as prostaglandin E$_2$ antagonists.

Specific compounds within the scope of the invention include, but are not limited to, the compounds discussed in the examples presented below, as well as their pharmaceutically-acceptable salts, esters, and amides.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and trans- geometric isomers, R- and S-enantiomers, diastereomers, d-isomers, l-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Certain compounds of the present invention may contain a basic functional group, such as amino, alkylamino or dialkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts," *J. Pharm. Sci.*, 66, 1-19 (1977), which, as well as all other documents referred to herein, is incorporated herein by reference.)

In other cases, the compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S.M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal, or for producing some other therapeutic effect, as discussed in more detail hereinbelow, comprising administering a therapeutically-effective amount of a compound of Formula I, as described hereinabove, to the animal.

The preferred embodiments of this invention are the compounds described in Examples 8, 9, 11, 13, 14, 16, 20 and 21 below. The most preferred embodiment of the invention is the compound described in Example 20 below.

(3) Utility

Compounds of the present invention exhibit activity as prostaglandin $E_2$ antagonists (prostaglandin antagonists of the $E_2$ series).

Compounds within the present invention, and the pharmaceutical compositions comprising one or more of these compounds, are useful as analgesic agents for the elimination or amelioration of pain in animals.

In addition to treating pain, these compounds and compositions would be useful in treating convulsions, ischemia and other central nervous system disorders, as well as osteoporosis, dysmenorrhea, asthma, enuresis, arrhythmia, urinary incontinence, gastric hypermotility, irritable bowel syndrome and diarrhea, by virtue of their activity as prostaglandin $E_2$ antagonists.

(4) Methods of Preparation

In general, the compounds of the present invention may be prepared by the methods illustrated in the following general reaction schemes, or by modifications thereof, using readily available starting materials, reagents and conventional synthesis procedures. Unless otherwise specified, the various substituents of the compounds are defined in the same manner as they are defined above in Formula I in the "Summary of Invention" section.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In each of the General Reaction Schemes, urea may be synthesized by reacting the title compound (product) of Example 13 hereinbelow with the appropriate isocyanate, as known by those of skill in the art. In addition, urethane may be synthesized by combining the appropriately-substituted chloroformate, which is commercially available, with the title compound (product) of Example 13. Phosphonate may be synthesized by making the trifluoromethanesulfonate ester of the title compound (product) of Example 19 by standard techniques known by those of skill in the art, and reacting the resulting trifluoromethanesulfonate ester with a dialkylphosphite and palladium (0). The result is a phosphonate ester. One of ordinary skill in the art knows how to synthesize the various possible substitutions of the urea, urethane, phosphonate, as well as sulfonamide, which are discussed in the definition section of this specification, where each of these terms is defined.

In General Reaction Scheme No. 1, substituted salicaldehyde or thiosalicaldehyde (wherein X is oxygen or sulfur and wherein $R^2$ is hydrogen or halogen) is reacted with base, and to this is added substituted 2-chloronitrobenzene (wherein $R^1$ is hydrogen, hydroxy, alkyl, haloalkyl, alkoxy, carboxy, alkoxycarbonyl, amino, aminocarbonyl, alkylamino, dialkylamino, amido, halogen, cyano, nitro, trifluromethyl, sulfonamide, phosphonate, urea or urethane). The resulting ether (or thioether) is reduced to yield substituted dibenzoxazepine (dibenzothiazepine), wherein $R^1$ and $R^2$ are as described hereinabove. The nitrogen is functionalized to yield a diacylhydrazide. If dibenzothiazepine, oxidation of the sulfur is achieved with hydrogen peroxide.

In General Reaction Scheme No. 2, substituted salicaldehyde or thiosalicaldehyde (wherein X is oxygen or sulfur and wherein $R^2$ is hydrogen or halogen) is reacted with substituted 2-chloroaniline (wherein $R^1$ is as described in General Reaction Scheme No. 1). The resulting imine is reacted with base to form a tricycle. The resulting imine is reduced with $NABH_3CN$ to yield substituted dibenzoxazepine (dibenzothiazepine), wherein $R^1$ and $R^2$ are as described hereinabove. The nitrogen is functionalized to yield a diacylhydrazide. If dibenzothiazepine, oxidation of the sulfur is achieved with hydrogen peroxide.

In General Reaction Scheme no. 3, substituted phenol or thiophenol (wherein X is oxygen or sulfur and wherein $R^2$ is hydrogen or halogen) is reacted with base, and to this is added substituted 2-chloronitrobenzene (wherein $R_1$ is as described in General Reaction Scheme No. 1). The resulting ether (or thioether) is reduced to yield an amine. The amine is reacted with phosgene followed by aluminum chloride. The resulting lactam is reduced with lithium aluminum hydride. The nitrogen is functionalized to yield a diacylhydrazide, Wherein R¹ and R² are as described hereinabove. If dibenzothiazepine, oxidation of the sulfur is achieved with hydrogen peroxide.

In each of the three general reaction schemes, X represents oxygen or sulfur, each of which is commercially available.

GENERAL REACTION SCHEME NO. I (structures I through VII shown)

GENERAL REACTION SCHEME NO. II (structures VIII through XII shown)

-continued
GENERAL REACTION SCHEME NO. II

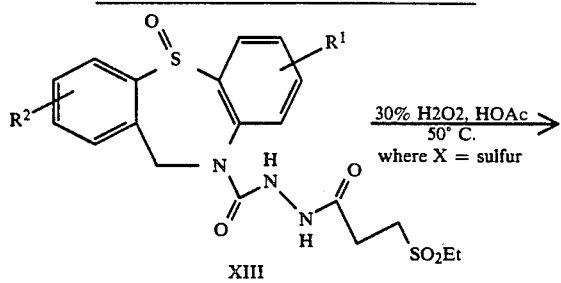
XIII

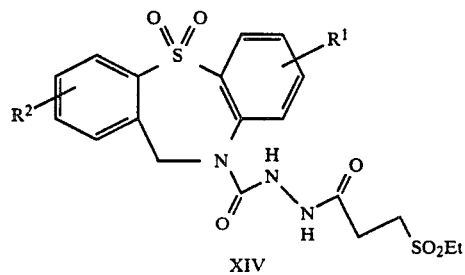
XIV

GENERAL REACTION SCHEME NO. III

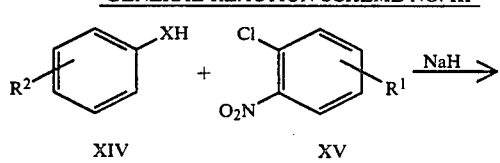
XIV    XV where X = oxygen or sulfur

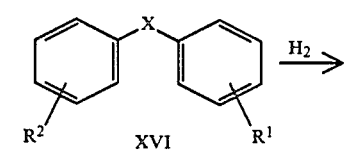
XVI

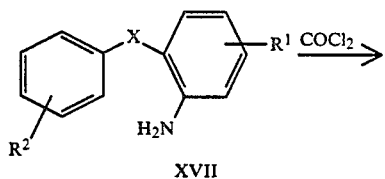
XVII

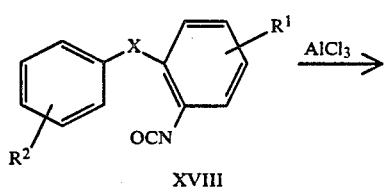
XVIII

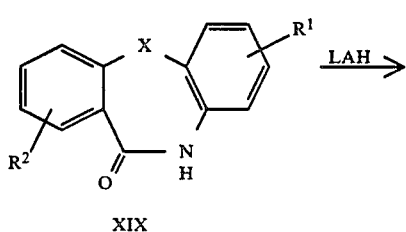
XIX

-continued
GENERAL REACTION SCHEME NO. III

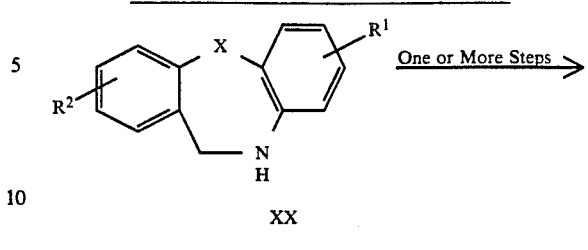
XX

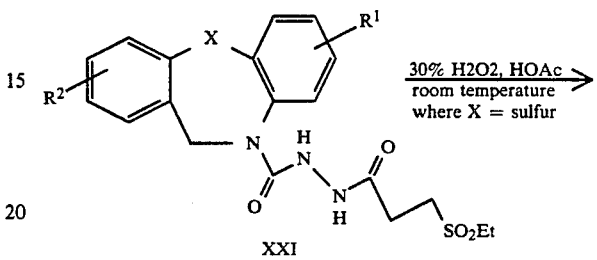
XXI

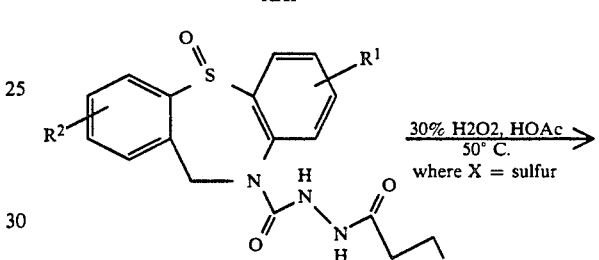
XXII

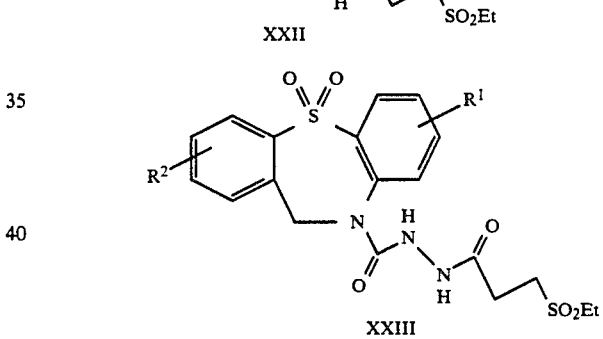
XXIII

The conditions for carrying out the individual steps in each of the general reaction schemes presented above are conventional, well-known, and capable of wide variation.

Other methods known in the art can also be used to synthesize the compounds of the present invention.

(5) Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfite, sodium metabisulfite, sodium sulfite and the like; (2) oil-soluble antioxidants, such as ascorbyl palmitate, butylated hydroxyanisole (BHA), butylated hydroxytoluene (BHT), propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I as described above), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

(6) Examples

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

All equipment employed in the examples is commercially available. Unless otherwise indicated, all starting materials employed in the examples are commercially available. Sources for these materials include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.) and Chemical Dynamics Corp. (South Plainfield, N.J.). Most of the starting materials were obtained from Aldrich Chemical Co. (Milwaukee, Wis.).

All patents and publications referred to in the examples, and throughout the specification, are hereby incorporated herein by reference, without admission that such is prior art.

EXAMPLE 1

Dibenz[b,f][1,4]oxazepine-8,10(11 H)-dicarboxylic acid, 8-methyl ester, 10-[2-[3-(ethylsulfonyl)-1-oxopropyl]hydrazide]

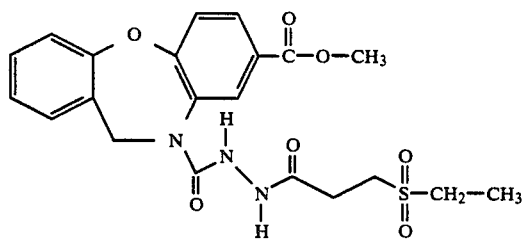

(a) Methyl 4-(2-formylphenoxy)-3-nitrobenzoate

Sodium hydride (3.09 g) was added in portions to a stirred solution of salicylaldehyde (14.3 g) in N,N-dimethylformamide (180 mL) under nitrogen. To the resulting dark solution was added methyl 4-chloro-3-nitrobenzoate (23.0 g) and N,N-dimethylformamide (50 mL), and the reaction was heated at 103° C. for 2.75 hours. The reaction was evaporated under vacuum, and the resulting oily mixture was partitioned between chloroform and water. The layers were separated, and the chloroform layer was washed with 1 M NaOH, water, and brine, dried over magnesium sulfate, and evaporated under vacuum to a yellow solid. Recrystalization from methanol yielded the title compound as light yellow crystals Mp: 109°-110° C.

b) Methyl 10,11-dihydrodibenz[b,f][1,4]oxazepine-8-carboxylate

The title compound of Example 1(a) (17 g) in tetrahydrofuran (150 mL) was shaken in a Parr hydrogenator at 5 psi hydrogen with Raney nickel at room temperature for 4 hours. The catalyst was filtered from the reaction, and the solution was evaporated under vacuum to an oil which crystallized on standing. Recrystallization from methanol yielded the title compound as white needles. Mp: 125°-126° C.

(c) Dibenz[b,f][1,4]oxazepine-8,10(11 H)-dicarboxylic acid, 8-methyl ester, 10-[2-[3-(ethylsulfonyl)-1-oxopropyl]-hydrazide]

Methyl 3-(ethylsulfonyl)propanoate was prepared in the manner described in "Sulfinic Acids. I.," *Chemical Abstracts*, 51(F03), 1064 (1956). The addition of sulfinic acids to an α,β-unsaturated compound (esters, ketones, amides, nitriles) results in sulfones. The reaction is conducted in an aqueous solution in the presence of $NaH_2PO_4$ (0.11 mole per 0.1 mole of Na salt of the sulfinic acid and 0.12 mole of the α,β-unsaturated compound in 200 mL of water).

To a stirring solution of methyl 3-(ethylsulfonyl)-propanoate (10 mmol) in ethanol (30 mL) was added hydrazine monohydrate (15 mmol), and the resulting solution was stirred for 16 hours. The resulting precipitate was collected to yield 2-[3-(ethylsulfonyl)-1-oxopropyl], hydrazide as a white solid (52%).

To a stirred solution of phosgene (1.93 M in toluene, .9.3 mL) in tetrahydrofuran (45 mL) at approximately 5° C. (ice water bath) under nitrogen was added dropwise a solution of the title compound of Example 1(b) (2.5 g) and triethylamine (1.5 mL) in tetrahydrofuran (30 mL). The ice bath was removed, and the reaction was stirred at ambient temperature for 1.5 hours. The reaction was then evaporated under vacuum, and to the resulting residue was added 2-[3-(ethylsulfonyl)-1-oxopropyl]hydrazide (1.76 g), triethylamine (1.5 mL) and toluene (50 mL). The reaction mixture was refluxed for 2 hours and cooled to room temperature. The precipitate was collected by filtration, washed with ether, suspended in water, and heated on a steam bath for 5 minutes. After cooling to room temperature, the insoluble product was collected by filtration and crystallized from methanol. Recrystallization from methanol yielded the pure title compound as a white solid. Mp: 172°-176° C.

EXAMPLE 2

Dibenz[b,f][1,4]oxazepine-7,10(11 H)-dicarboxylic acid, 7-methyl ester, 10-[2-[3-(ethylsulfonyl)-1-oxopropyl]hydrazide]

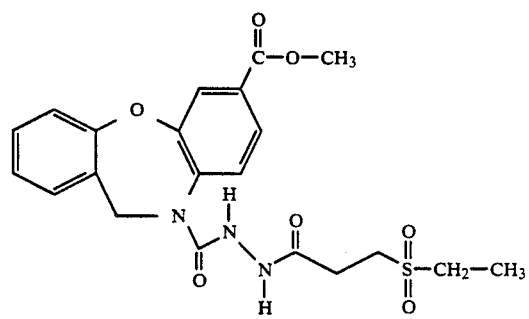

The title compound was prepared by the method described above for the preparation of the title compound of Example 1, with the exception that methyl 10,11-dihydrodibenz[b,f]oxazepine-7-carboxylate was employed in place of the title compound of Example 1(b).

EXAMPLE 3

Dibenz[b,f][1,4]oxazepine-8,10(11 H)-dicarboxylic acid, 8-(1,1-dimethylethyl) ester, 10-[2-[3-(ethylsulfonyl)-1-oxopropyl]hydrazide]

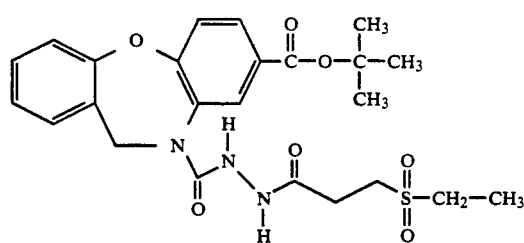

(a) 1,1-dimethylethyl 4-chloro-3-nitrobenzoate

A solution of n-butyl lithium (1.6 M, 101 mL) was added dropwise to stirring anhydrous tert-butanol (200 mL) under nitrogen in a room temperature water bath. After 0.5 hours, 4-chloro-3-nitrobenzoyl chloride (10.0 g) was added, and the dark solution was stirred for 1.5 hours at room temperature. The reaction was evaporated under vacuum, and the residue was crystallized from hexane to yield the title compound as an orange solid. Mp: 66°-67° C.

(b) 1,1-dimethylethyl 4-(2-formylphenoxy)-3-nitrobenzoate

Sodium hydride (0.79 g) was added in portions to a stirred solution of salicylaldehyde (3.83 g) in N,N-dimethylformamide (60 mL) under nitrogen. To the resulting dark solution was added the title compound of Example 3(a) (7.0 g), and the reaction was stirred at 100° C. for 2.5 hours. The reaction was evaporated under vacuum, and the residue was partitioned between chloroform and 1 M NaOH. The layers were separated, and the aqueous layer was extracted once more with chloroform. The combined chloroform extracts were washed with 1 M NaOH, water and brine, dried over magnesium sulfate, and evaporated under vacuum to a dark oil. Flash chromatography through silica gel 60 using 2:1 chloroform:hexane yielded the title compound as a thick, yellow oil.

(c) 1,1-dimethylethyl 10,11-dihydrodibenz[b,f][1,4]oxazepine-8-carboxylate

The title compound of Example 3(b) (4.8 g) in tetrahydrofuran (160 mL) was shaken in a Parr hydrogenator at 30 psi hydrogen with Raney nickel at room temperature for 4 hours. The catalyst was filtered from the reaction, and the solution was evaporated under vacuum. Flash chromatography through silica gel 60 using 9:1 hexane:ethyl acetate yielded the title compound as a yellow solid. Mp: 121°–123° C.

(d) Dibenz[b,f][1,4]oxazepine-8,10(11 H)-dicarboxylic acid, 8-(1,1-dimethylethyl) ester. 10-[2-[3-(ethylsulfonyl) -1-oxopropyl]hydrazide]

To a stirred solution of phosgene (1.93 M in toluene, 6.7 mL) in tetrahydrofuran (30 mL) at approximately 5° C. (ice water bath) under nitrogen was added dropwise a solution of the title compound of Example 3(c) (2.0 g) and triethylamine (1.0 mL) in tetrahydrofuran (20 mL). The ice bath was removed, and the reaction was stirred at ambient temperature for hour. The reaction was evaporated under vacuum, and to the resulting residue was added 2-[3-(ethylsulfonyl)-1-oxopropyl]hydrazide (1.22 g), triethylamine (1.0 mL) and toluene (40 mL). The resulting mixture was refluxed for 2.5 hours, and evaporated under vacuum. The residue was partitioned between chloroform and water, the layers were separated, and the chloroform layer was washed with water, saturated sodium bicarbonate, and brine. After drying over magnesium sulfate, the solution was evaporated under vacuum. The crude product was flash chromatographed through silica gel 60 using 3:1 chloroform:tetrahydrofuran to yield a thick oil. The oil was placed under vacuum at room temperature to yield the title compound as a solidified white foam. HPLC: 99.66% pure.

EXAMPLE 4

Dibenz[b,f][1,4]oxazepine-8,10(11 H)-dicarboxylic acid, 10-[2-[3-(ethylsulfonyl)-1-oxopropyl]hydrazide]

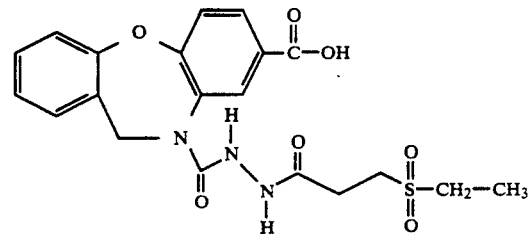

A solution of the title compound of Example 3(d) (2.05 g), HCl (6.9 M in dioxane, 35 mL), and glacial acetic acid (35 mL) were stirred together at room temperature for 2.5 hours. The reaction was evaporated under vacuum, pentane was added, and the mixture was again evaporated under vacuum. The residue was dissolved in a minimal amount of tetrahydrofuran and treated with pentane to force the product out of solution. The mixture was evaporated under vacuum, and the semi-solid residue was chromatographed through a medium pressure liquid chromatography column packed with acidic silica gel, using tetrahydrofuran. After crystallization from tetrahydrofuran/pentane, the yellowish product was washed with tetrahydrofuran, hexane and then ether to yield the title compound as a white solid. Mp: 191°–194° C.

EXAMPLE 5

Dibenz[b,f][1,4]oxazepine-7,10(11 H)-dicarboxylic acid, 1,1-(dimethylethyl) ester, 10-[2-[3-(ethylsulfonyl)-1-oxopropyl]hydrazide]

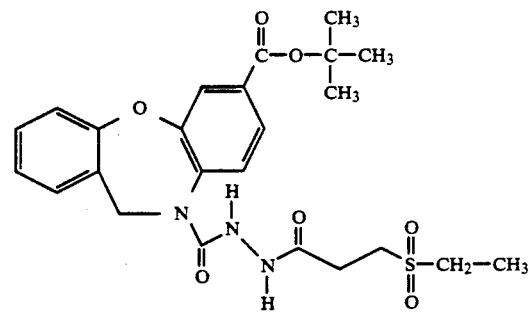

The title compound was prepared by the method described above for the preparation of the title compound of Example 3, with the exception that 3-chloro-4-nitrobenzoyl chloride was employed in place of 4-chloro-3-nitrobenzoyl chloride as the starting material.

EXAMPLE 6

Dibenz[b,f][1,4]oxazepine-7,10(11 H)-dicarboxylic acid, 10-[2-[3-(ethylsulfonyl)-1-oxopropyl]hydrazide]

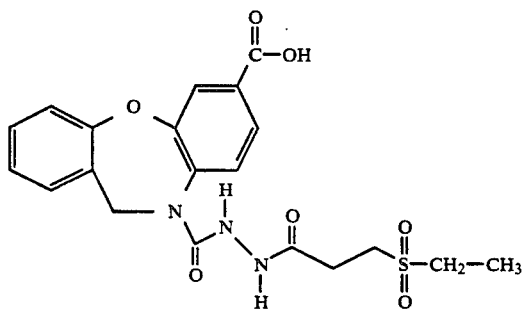

The title compound was prepared by the method described above for the preparation of the title compound of Example 4, with the exception that dibenz[b,f][1,4]oxazepine-7,10(11 H)-dicarboxylic acid, 7(1,1-dimethylethyl) ether, 10-[2-[3-(ethylsulfonyl)-1-oxopropyl]hydrazide] was employed in place of the title compound of Example 3(d) as the starting material.

EXAMPLE 7

8-fluorodibenz[b,f][1,4]oxazepine-10(11 H)-carboxylic acid, 2-[3-(ethylsulfonyl)-1-oxopropyl]hydrazide

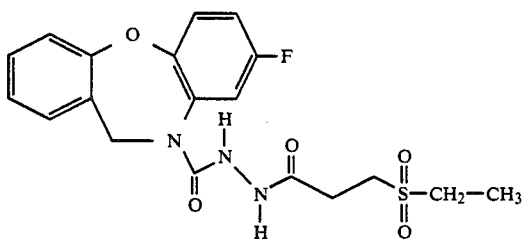

(a) 2-(4-fluoro-2-nitrophenoxy)benzaldehyde

Sodium hydride (1.66 g) was added in portions to a stirred solution of salicylaldehyde (8.06 g) in N,N-dimethylformamide (100 mL) under nitrogen. To the resulting yellow solution was added 2,5-difluoro-1-nitrobenzene (10.0 g) and N,N-dimethylformamide (10 mL). The reaction was heated at 50° C. for 18 hours and evaporated under vacuum. The oily mixture was taken up in chloroform, and washed with 1 M NaOH, water, 1 M HCl, and brine, dried over magnesium sulfate, and evaporated under vacuum to an orange oil. The oil was treated with ethyl ether, cooled in an ice bath, and the precipitated product was collected by filtration to yield the title compound as white crystals. Mp: 94°–95° C.

(b) 8-fluoro-10,11-dihydrodibenz[b,f][1,4]oxazepine

The title compound of Example 7(a) (5.0 g) in 1:1 methanol:ethyl acetate (200 mL) was shaken in a Parr Hydrogenator at 30 psi hydrogen with Raney nickel at room temperature for 13.75 hours. The catalyst was filtered from the reaction, and the solution was evaporated under vacuum. The residue was flash chromatographed through silica gel 60 using chloroform to yield the title compound as a white solid. Mp: 94° C.

(c) 8-fluorodibenz[b,f][1,4]oxazepine-10(11 H)-carboxylic acid, 2-[3-(ethylsulfonyl)-1-oxopropyl]hydrazide To a stirred solution of phosgene (1.93 M in toluene, 93 mL) in tetrahydrofuran (40 mL) at approximately 5° C. (ice water bath) under nitrogen was added dropwise a solution of the title compound of Example 7(b) (2.0 g) and triethylamine (1.4 mL) in tetrahydrofuran (30 mL). The ice bath was removed, and the reaction was stirred at ambient temperature for 1 hour. The reaction was evaporated under vacuum, and to the residue was added 2-[3-(ethylsulfonyl)-1-oxopropyl]hydrazide (1.68 g), triethylamine (1.4 mL) and toluene (55 mL). The reaction mixture was refluxed under nitrogen for 3 hours, and stirred at room temperature overnight. The mixture was evaporated under vacuum, and the residue was stirred with a mixture of chloroform (125 mL) and 1 M HCl (125 mL). The bi-phasic mixture was filtered to collect the undissolved product. The chloroform layer was washed with brine, dried over magnesium sulfate, and evaporated under vacuum. This was combined with the undissolved product collected previously, washed with ethyl ether, and crystallized from ethanol (3A) to yield the title compound as a white solid. Mp: 191°–193° C.

EXAMPLE 8

2-chlorodibenz[b,f][1,4]oxazepine-10(11 H)-carboxylic acid, 2-[3-(ethylsulfonyl)-1-oxopropyl]hydrazide

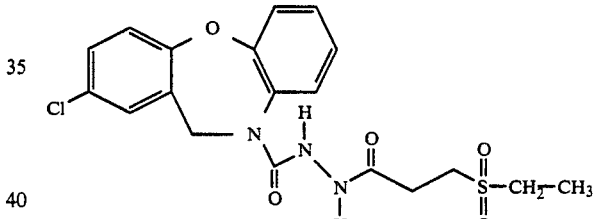

(a) 5-chloro-2-(2-nitrophenoxy)benzaldehyde

To a stirred solution of 5-chlorosalicylaldehyde (4.00 g) in N,N-dimethylformamide (40 mL) under nitrogen was added sodium hydride in portions (0.64 g). To the resulting reddish solution was added a solution of 1-fluoro-2-nitrobenzene (3.50 g) in N,N-dimethylformamide (10 mL) in one lot. The reaction was then stirred at 63° C. under nitrogen for 24 hours. The reaction was evaporated under vacuum, and the residue was partitioned between chloroform and 1 N NaOH. The layers were separated, and the aqueous layer was extracted once more with chloroform. The combined chloroform extracts were washed with 1 N NaOH, water, 1 N HCl, water, and brine, dried over magnesium sulfate, and evaporated under vacuum. The residue was crystallized from cyclohexane to yield the title compound as a light yellow solid. Mp: 103°–105° C.

(b) 2-chloro-10,11-dihydrodibenz[b,f][1,4]oxazepine

A solution of the title compound of Example 8(a) (2.00 g) in tetrahydrofuran (100 mL) was shaken over Raney Nickel in a Parr Hydrogenator at 5 psi hydrogen. The catalyst was removed by filtration, and the filtrate was evaporated under vacuum. Flash chromatography on a medium pressure liquid chromatography system through silica gel 60 using 2:1 chloroform:hexane yielded the desired title compound as a yellow solid. Mp: 123°-125° C.

(c) 2-chlorodibenz[b,f][1,4]oxazepine-10(11 H)-carboxylic acid, 2-[3-(ethylsulfonyl)-1-oxopropyl]hydrazide To a cold (ice water bath) solution of phosgene (1.93 M in toluene, 3.5 mL) and tetrahydrofuran (15 mL) under nitrogen was added dropwise a solution of the title compound of Example 8(b) (0.75 g) and triethylamine (0.53 mL) in tetrahydrofuran (12 mL). The resulting mixture was stirred for 90 minutes at room temperature, and the reaction was evaporated under vacuum. To the residue was added 2-[3-(ethylsulfonyl)-1-oxopropyl]hydrazide (0.61 g), triethylamine (0.53 mL) and toluene (20 mL), and the reaction was refluxed under nitrogen for 3.5 hours, and then stirred at room temperature overnight. The reaction mixture was diluted with ethyl ether, and the solid was collected by filtration. The solid was washed with ethyl ether, and was suspended in water (25 mL). After heating on a steam bath for 5 minutes, the undissolved product was collected by filtration, washed with water followed by ethyl ether, and air dried. Flash chromatography through silica gel 60 using 3:1 chloroform: tetrahydrofuran followed by crystallization from ethanol (3A) yielded the desired title compound as a white solid. Mp: 184°-185° C.

EXAMPLE 9

2.8-dichlorodibenz[b,f][1,4]oxazepine-10(11 H)-carboxylic acid, 2-[3-(ethylsulfonyl)-1-oxopropyl]hydrazide

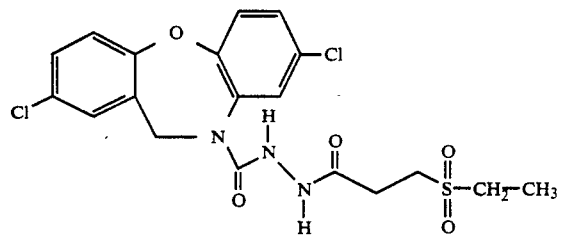

(a) 5-chloro-2-(4-chloro-2-nitrophenoxy)benzaldehyde

To a stirred solution of 5-chlorosalicylaldehyde (8.56 g) in N,N-dimethylformamide (90 mL) under nitrogen was added, in portions, sodium hydride (1.37 g). To the resulting solution was added 2,5-dichloro-1-nitrobenzene (10.0 g) and N,N-dimethylformamide (10 mL), and the reaction was heated at 100° C. under nitrogen for 6 hours. The reaction was evaporated under vacuum, and the residue was partitioned between chloroform and 1 N NaOH. The layers were separated, and the aqueous layer was extracted once more with chloroform. The combined chloroform extracts were washed with 1 N NaOH, water, 1 N HCl, water, and brine, dried over magnesium sulfate, and evaporated under vacuum. Crystallization from methanol yielded the title compound as a yellow solid. Mp: 128°-130° C.

(b) 2.8-dichloro-10,11-dihydrodibenz[b,f][1,4]-oxazepine

A solution of the title compound of Example 9(a) (2.00 g) in tetrahydrofuran (100 mL) was shaken over Raney Nickel in a Parr Hydrogenator at 5 psi hydrogen. The catalyst was removed by filtration, and the filtrate was evaporated under vacuum. Flash chromatography on a medium pressure liquid chromatography system through silica gel 60 using 1:1 chloroform:hexane yielded the desired title compound as a yellow solid. Mp: 103°-105° C.

(c) 2,8-dichlorodibenz[b,f][1,4]oxazepine-10(11 H)-carboxylic acid, 2-[3-(ethylsulfonyl)-1-oxopropyl]hydrazide To a cold (ice water bath) solution of phosgene (1.93 M in toluene, 1.2 mL) and tetrahydrofuran (6 mL) under nitrogen was added dropwise a solution of the title compound of Example 9(b) (0.28 g) and triethylamine (0.18 mL) in tetrahydrofuran (4 mL). The resulting mixture was stirred for 30 minutes at room temperature, and then refluxed on a steam bath for 1 hour. The reaction was evaporated under vacuum, and to the residue was added 2-[3-(ethylsulfonyl)-1-oxopropyl]hydrazide (0.21 g), triethylamine (0.18 mL) and toluene (7 mL), and the reaction was refluxed under nitrogen for 3 hours, and then stirred at room temperature overnight. The reaction mixture was diluted with ethyl ether, and the solid was collected by filtration. The solid was washed with ethyl ether followed by 1 N HCl, and then again with ethyl ether. This was flash chromatographed through silica gel 60 using 95:5 chloroform:methanol. The resulting residue was triturated with ethanol (3A), diluted with isopropyl ether, and the solid was collected by filtration to yield the title compound as a white solid. Mp: 189°-190° C.

EXAMPLE 10

8-nitrodibenz[b,f][1,4]oxazepine-10(11 H)-carboxylic acid, 2-[3-(ethylsulfonyl)-1-oxopropyl]hydrazide

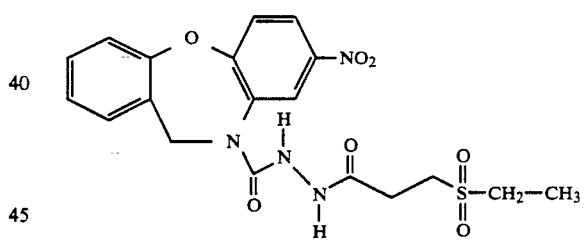

(a) 2-[[(2-chloro-5-nitrophenyl)imino]methyl]phenol

A solution of salicylaldehyde (30.0 g) and 2-chloro-5-nitroanaline (42.5 g) in ethanol (3A, 600 mL) was heated at reflux for 3 hours. The resulting mixture was cooled to 0° C. for one hour, and the product was collected by filtration, washed with cold ethanol followed by hexane, and air dried to yield the title compound as orange crystals. Mp: 168°-169° C.

(b) 8-nitrodibenz[b,f][1,4]oxazepine

Sodium hydride (5.71 g) was added in portions to a stirred solution of the title compound of Example 10(a) (59.3 g) in N,N-dimethylformamide (550 mL) under nitrogen at 53° C. After stirring for 2 hours at 53° C., the resulting mixture was evaporated under vacuum to a volume of approximately 150 mL, and water (1 L) was added. The precipitated product was collected by filtration and rinsed twice with water. The wet, crude product was taken up in hot ethyl acetate, dried over magnesium sulfate while hot, filtered, and allowed to cool.

The crystallized product was collected by filtration and washed with cold ethanol (3A) followed by hexane to yield the title compound as a tan solid. Mp: 179°–181° C.

(c) 10,11-dihydro-8-nitrodibenz[b,f][1,4]oxazepine

To a stirred mixture of the title compound of Example 10(b) (24.0 g) and sodium cyanoborohydride (6.72 g) in absolute ethanol (480 mL) was added concentrated hydrochloric acid until a pH of 4 was achieved. The reaction was stirred at room temperature for 2.5 hours, adding concentrated hydrochloric acid as necessary to maintain the pH between 3.5 and 4.0. The reaction was evaporated under vacuum to remove about two thirds of the volume, and was then poured into saturated sodium bicarbonate. The resulting mixture was extracted with chloroform, and the chloroform extract was washed with saturated sodium bicarbonate and brine, dried over magnesium sulfate, and evaporated under vacuum. Recrystallization from toluene yielded the title compound as orange crystals. Mp: 154°–156° C.

(d) 8-nitrodibenz[b,f][1,4]oxazepine-10(11 H)-carboxylic acid, 2-[3-(ethylsulfonyl)-1-oxopropyl]hydrazide To a stirred solution of phosgene (1.93 M in toluene, 15.6 mL) in tetrahydrofuran (65 mL) at approximately 5° C. (ice water bath) under nitrogen was added dropwise a solution of the title compound of Example 10(c) (4.0 g) and triethylamine (2.4 mL) in tetrahydrofuran (40 mL). The ice bath was removed, and the reaction was stirred at ambient temperature for 1.5 hours. The reaction was evaporated under vacuum, and to the residue was added 2-[3-(ethylsulfonyl)-1-oxopropyl]hydrazide (3.0 g), triethylamine (2.4 mL) and toluene (80 mL). The reaction mixture was refluxed for 2 hours, cooled to room temperature, diluted with ether, and the precipitate was collected by filtration. After washing with ether, the precipitate was suspended in water, heated on a steam bath for 5 minutes, and cooled to room temperature. The insoluble product was collected by filtration, washed with water followed by ether, and recrystallized from ethanol (3A) to yield the title compound as white needles. Mp: 198°–200° C.

EXAMPLE 11

8-cyanodibenz[b,f][1,4]oxazepine-10(11 H)-carboxylic acid, 2-[3-(ethylsulfonyl)-1-oxopropyl]hydrazide

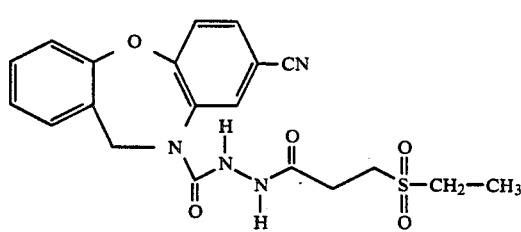

(a) 4-chloro-3-[[(2-hydroxyphenyl)-methylene]amino]benzonitrile

A solution of salicylaldehyde (4.80 g) and 2-chloro-5-cyanoanaline (6.0 g) in ethanol (3A, 150 mL) was heated at reflux for 3 hours. The resulting mixture was cooled to room temperature overnight, and the product was collected by filtration, washed with cold ethanol, and air dried to yield the title compound as a yellow solid. Mp: 147°–148° C.

(b) Dibenz[b,f][1,4]oxazepine-8-carbonitrile

Sodium hydride (0.47 g) was added in portions to a stirred solution of the title compound of Example 11(a) (4.50 g), and a catalytic amount of copper powder in N,N-dimethylformamide (50 mL) under nitrogen. The reaction was heated to 100° C. and stirred for 3 hours. The resulting mixture was evaporated under vacuum and partitioned between chloroform and water. The layers were separated, and the water layer was extracted once more with chloroform. The combined chloroform extracts were washed with water and brine, dried over magnesium sulfate, and evaporated under vacuum to a brown solid. Recrystallization from ethanol (3A) yielded the title compound as yellow needles. Mp: 158°–159° C.

(c) 10,11-dihydrodibenz[b,f][1,4]oxazepine-8-carbonitrile

To a stirred mixture of the title compound of Example 11(b) (1.60 g) and sodium cyanoborohydride (0.49 g) in absolute ethanol (35 mL) was added concentrated hydrochloric acid until a pH of 4 was achieved. The reaction was stirred at room temperature for 2.5 hours, adding concentrated hydrochloric acid as necessary to maintain the pH between 3.5 and 4.0. The reaction was evaporated under vacuum, and the residue was partitioned between saturated sodium bicarbonate and chloroform. The layers were separated and the chloroform layer was washed with saturated sodium bicarbonate, water, and brine, dried over magnesium sulfate, and evaporated under vacuum to a yellow solid. Flash chromatography through silica gel 60 using chloroform yielded the title compound as a white solid. Mp: 104°–105° C.

(d) 8-cyanodibenz[b,f][1,4]oxazepine-10(11 H)-carboxylic acid, 2-[3-(ethylsulfonyl)-1-oxopropyl]hydrazide To a stirred solution of phosgene (1.93 M in toluene, 4.3 mL) in tetrahydrofuran (18 mL) at approximately 5° C. (ice water bath) under nitrogen was added dropwise a solution of the title compound of Example 11(c) (1.0 g) and triethylamine (0.65 mL) in tetrahydrofuran (11 mL). The ice bath was removed, and the reaction was stirred at ambient temperature for one hour. The reaction was evaporated under vacuum, and to the residue was added 2-[3-(ethylsulfonyl)-1 -oxopropyl]hydrazide (0.82 g), triethylamine (0.65 mL) and toluene (22 mL). The reaction mixture was refluxed for 2 hours, cooled to room temperature, diluted with ether, and the precipitate was collected by filtration. After washing with ether, the precipitate was suspended in water, heated on a steam bath for 5 minutes, and cooled to room temperature. The insoluble product was collected by filtration, washed with water followed by ether, and recrystallized from ethanol (3A) to yield the title compound as white needles. Mp: 188°–190° C.

EXAMPLE 12

6-chlorodibenz[b,f][1,4]oxazepine-10(11 H)-carboxylic acid, 2-[3-(ethylsulfonyl)-1-oxopropyl]hydrazide

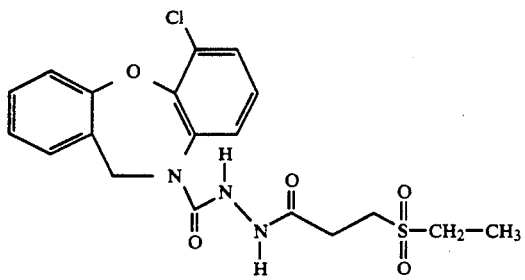

(a) 2-[[(2,3-dichlorophenyl)imino]methyl]phenol

Salicylaldehyde (11.31 g) and 2,3-dichloroanaline (15.00 g) were refluxed in absolute ethanol (100 mL) under nitrogen for 3 hours. The reaction was cooled to room temperature, and the precipitated product was collected by filtration, washed with ethanol, and pressed to remove as much solvent as possible. The product was dried under vacuum at 56° C. to produce the title compound as a yellow solid. Mp: 89°–90° C.

(b) 6-chlorodibenz[b,f][1,4]oxazepine

To a stirred solution of the title compound of Example 12(a) (5.00 g) in N,N-dimethylformamide (50 mL) under nitrogen was added in portions sodium hydride (0.50 g), a catalytic amount of copper powder, and N,N-dimethylformamide (50 mL). The reaction was stirred at 100° C. under nitrogen for 3 hours, and then at 150° C. overnight. The reaction was evaporated under vacuum, and the residue was partitioned between chloroform and water. The layers were separated, and the aqueous layer was extracted once more with chloroform. The combined chloroform extracts were washed with water and brine, dried over magnesium sulfate, and evaporated under vacuum to a dark red oil. Flash chromatography through silica gel 60 using chloroform yielded the title compound as a thick, yellow oil.

(c) 6-chloro-10,11-dihydrodibenz[b,f][1,4]oxazepine

To a stirred mixture of the title compound of Example 12(b) (2.00 g) and sodium cyanoborohydride (0.59 g) in absolute ethanol (40 mL) was added concentrated hydrochloric acid until a pH of 4 was achieved. The reaction was stirred at room temperature for 4 hours adding concentrated hydrochloric acid as necessary to maintain the pH between 3 and 4. The reaction was evaporated under vacuum, and the residue was partitioned between saturated sodium bicarbonate and chloroform. The layers were separated, and the aqueous layer was extracted once more with chloroform. The combined chloroform extracts were washed with saturated sodium bicarbonate, water, and brine, dried over magnesium sulfate, and evaporated under vacuum. Flash chromatography through silica gel 60 using 4:1 chloroform:hexane yielded the title compound as a yellow oil.

(d) 6-chlorodibenz[b,f][1,4]oxazepine-10(11 H)-carboxylic acid, 2-[3-(ethylsulfonyl)-1-oxopropyl]hydrazide To a stirred solution of phosgene (1.93 M in toluene, 6.5 mL) in tetrahydrofuran (30 mL) at approximately 5° C. (ice water bath) under nitrogen was added dropwise a solution of the title compound of Example 12(c) (1.50 g) and triethylamine (1.0 mL) in tetrahydrofuran (20 mL). The ice bath was removed, and the reaction was stirred at ambient temperature for 2 hours. The reaction was evaporated under vacuum, and to the residue was added 2-[3-(ethylsulfonyl)-1-oxopropyl]hydrazide (1.28 g), triethylamine (1.0 mL) and toluene (35 mL). The reaction mixture was refluxed for 2.5 hours, cooled to room temperature, diluted with ether, and the precipitate was collected by filtration. After washing with ether, the precipitate was suspended in water, heated on a steam bath for 5 minutes, and cooled to room temperature. The insoluble product was collected by filtration and washed with water followed by ether. Chromatography yielded the desired title compound as a white solid. Mp: 209°–211° C.

EXAMPLE 13

8-aminodibenz[b,f][1,4]oxazepine-10(11 H)-carboxylic acid, 2-[3-(ethylsulfonyl)-1-oxopropyl]hydrazide

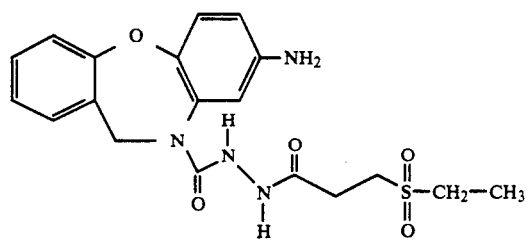

A solution of the title compound of Example 10 (4.0 g) in tetrahydrofuran (250 mL) was shaken in a Parr Hydrogenator at 38 psi hydrogen over 5% palladium on carbon for 18 hours. The catalyst was filtered from the reaction, and the solution was evaporated under vacuum. Crystallization of the residue from ethanol (3A) yielded the title compound as a yellow solid. Recrystallization of this from ethanol (3A) yielded the pure title compound as yellow crystals. Mp: 172°–179° C.

EXAMPLE 14

8-[(methylsulfonyl)amino]dibenz[b,f][1,4]-oxazepine-10(11 H)-carboxylic acid, 2-[3-(ethylsulfonyl)-1-oxopropyl]hydrazide

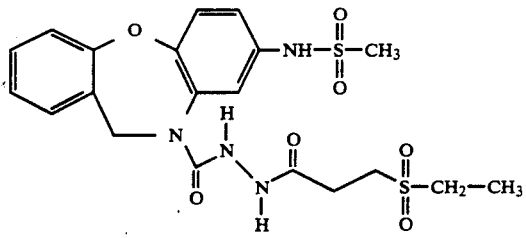

To a stirred solution of the title compound of Example 13 (1.0 g) in pyridine (15 mL) under nitrogen at approximately 5° C. (ice water bath) was added dropwise via syringe methanesulfonyl chloride (0.28 mL). The ice bath was removed, and the reaction was stirred at ambient temperature for 2 hours. The reaction was then evaporated under vacuum, and the residue was treated with 1 M HCl. The insoluble product was collected by filtration, washed twice with 1 M HCl, and then with water. The solid was suspended in methanol, heated to reflux on a steam bath, cooled to room temperature, and the product was collected by filtration. Recrystallization from acetonitrile yielded the title compound as a pinkish solid. Mp: 211°-212° C.

EXAMPLE 15

8-(diethylamino)dibenz[b,f][1,4]oxazepine-10(11H)-carboxylic acid, 2-[3-(ethylsulfonyl)-1-oxopropyl]hydrazide

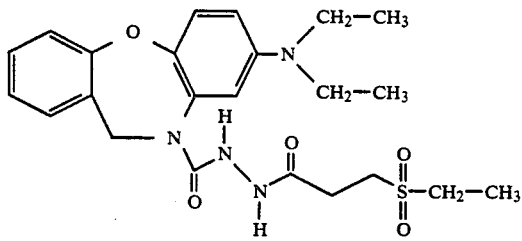

To a stirred solution of the title compound of Example 13 (2.0 g), acetaldehyde (3.0 mL), sodium cyanoborohydride (0.904 g), and water (2.6 mL) in acetonitrile (20 mL) was added glacial acetic acid (0.5 mL) over a period of 6 minutes. The reaction was stirred for 2.5 hours at ambient temperature, and then glacial acetic acid was added (0.5 mL), and the reaction was stirred for an additional 30 minutes. The resulting mixture was evaporated under vacuum, and the residue was partitioned between ethyl acetate and saturated sodium bicarbonate. The layers were separated, and the aqueous layer was extracted once more with ethyl acetate. The combined ethyl acetate extracts were washed with brine, dried over magnesium sulfate, and evaporated under vacuum to a clear, greenish oil. The oil was chromatographed four times: twice through silica gel 60 using 97:3 ethyl acetate:ethanol; next through silica gel 60 using 3:1 chloroform:tetrahydrofuran; and finally through reverse phase silica gel (C18) using 80:20:1 acetonitrile:water:ammonium hydroxide. The product from the last column was co-evaporated three times with ethanol to azeotrope water from the product and dried under vacuum at room temperature to yield the title compound as a white solid containing 1.86% water. HPLC: 99.53% pure.

EXAMPLE 16

8-methoxydibenz[b,f][1,4]oxazepine-10(11H)-carboxylic acid, 2-3-(ethylsulfonyl)-1-oxopropyl]hydrazide

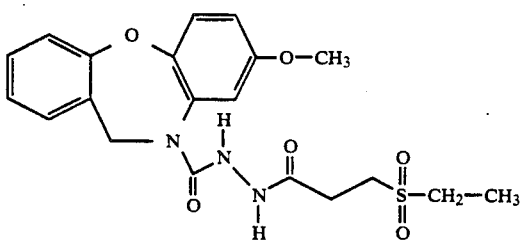

(a) 4-methoxy-2-nitro-1-phenoxybenzene

Sodium hydride (2.30 g) was added in portions to a solution of phenol (8.23 g) in N,N-dimethyl formamide (100 mL) in a room temperature water bath under nitrogen. The water bath was removed, and to the dark solution was added copper powder (0.74 g), 4-bromo-3-nitroanisole (13.54 g) and N,N-dimethylformamide (25 mL). The mixture was heated to 125° C. for 3 hours, and then evaporated under vacuum. The residue was partitioned between ether and 1 M NaOH and filtered through celite. The biphasic filtrate was separated, and the ethereal layer was washed with 1 N NaOH, water, and brine, dried over magnesium sulfate, and evaporated under vacuum. The crude oil was distilled under vacuum, and a fraction boiling at 155° C. (0.1 mm Hg) was collected. The impure fractions were combined with the pot residue and flash chromatographed through silica gel 60 using 4:1 chloroform:hexane. The distilled product and chromatographed product were combined to yield the title compound as an orange oil.

(b) 5-methoxy-2-phenoxybenzeneamine

A solution of the title compound of Example 16(a) (8 g) in methanol (70 mL) was shaken in a Parr Hydrogenator over 5% palladium on carbon at 5 psi hydrogen at room temperature for 6.75 hours. The catalyst was filtered from the reaction, and the solution was evaporated under vacuum. Flash chromatography through silica gel 60 using chloroform yielded the title compound as a yellow solid. Mp: 112°-114° C.

(c) 8-methoxydinenz[b,f][1,4]oxazepin-11(10H)-one

To a solution of phosgene (1.93 M in toluene, 60 mL) in toluene (90 mL) under nitrogen at approximately 5° C. was added, in portions, the title compound of Example 16(b) (5.0 g). The resulting solution was stirred at 0°-5° C. for 45 minutes, and then heated on a steam bath for 45 minutes under nitrogen. Evaporation under vacuum yielded the isocyanate compound as a clear oil. IR: 2250 cm (strong). The isocyanate compound was taken up in bromobenzene (40 mL) and added dropwise to a stirred mixture of aluminum chloride (3.10 g) in bromobenzene (80 mL) at 100° C. under nitrogen. The reaction temperature was raised to 150° C., and the reaction was stirred for one hour. The reaction was poured into ice/water (250 g) and filtered. The layers of the biphasic filtrate were separated, and the organic layer was evaporated under vacuum. The aqueous filtrate was extracted once with ethyl acetate, and the ethyl acetate extract was then combined with the residue from the evaporated organic layer. The resulting solution was washed with water, saturated sodium bicarbonate, water, 1 N HCl, and brine, dried over magnesium sulfate, and evaporated under vacuum. Flash chromatography through silica gel 60 using 4:1 chloroform:ethyl acetate yielded the title compound as a white solid. Mp: 164°-165° C.

(d) 10,11-dihydro-8-methoxydibenz[b,][1,4]oxazepine

A solution of lithium aluminum hydride (1.0 M in tetrahydrofuran, 34 mL) was added dropwise under nitrogen to a stirred solution of the title compound of Example 16(c) (2.7 g) in tetrahydrofuran (60 mL) in an ice water bath keeping the temperature below 10° C. The ice bath was removed, and the reaction was stirred at reflux for 4.5 hours. The resulting mixture was cooled to approximately 1° C. and quenched by the successive addition of water (1.3 mL), 15% NaOH (1.3 mL), and water (3.9 mL). The reaction was filtered through celite, and the filtrate was evaporated under vacuum to a light orange solid. Flash chromatography through silica gel 60 using 3:1 hexane:ethyl acetate yielded the title compound as a pinkish-white solid. Mp: 110°–112° C.

(e) 8-methoxydibenz[b,f][1,4]oxazepine-10(11 H)-carboxylic acid, 2-[3-(ethylsulfonyl)-1-oxopropyl]hydrazide To a stirred solution of phosgene (1.93 M in toluene, 8.4 mL) in tetrahydrofuran (40 mL) at approximately 5° C. (ice water bath) under nitrogen was added dropwise a solution of the title compound of Example 16(d) (2.00 g) and triethylamine (1.3 mL) in tetrahydrofuran (15 mL). The ice bath was removed, and the reaction was stirred at ambient temperature for 1.5 hours. The reaction was evaporated under vacuum, and to the residue Was added 2-[3-(ethylsulfonyl)-1-oxopropyl]hydrazide (1.59 g), triethylamine (1.3 mL), and toluene (50 mL). The reaction mixture was refluxed for 2 hours, stirred for 16 hours at room temperature, and then evaporated under vacuum. The residue was partitioned between ethyl acetate and 1 M HCl, and the undissolved product was collected by filtration, washed with 1 N HCl, water, and ether, and set aside. The layers of the biphasic filtrate were separated, and the aqueous layer was extracted once more with ethyl acetate. The ethyl acetate extracts were combined and washed with 1 M HCl, water, saturated sodium bicarbonate, and brine, dried over magnesium sulfate, and evaporated under vacuum. This was combined with the undissolved product collected earlier and recrystallized from ethanol (3A) to yield the pure title compound as white crystals. Mp: 187°–190° C.

EXAMPLE 17

8-methyldibenz[b,f][1,4]oxazepine-10(11 H)-carboxylic acid, 2-[3-(ethylsulfonyl)-1-oxopropyl]hydrazide

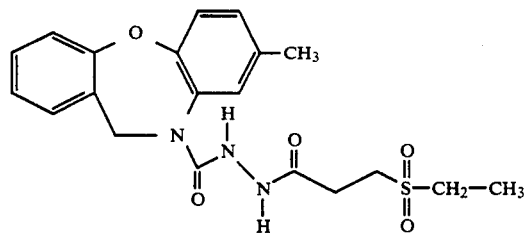

4-methyl-2-nitro-1-phenoxybenzene

Sodium hydride (2.94 g) was added in portions to a solution of phenol (10.97 g) in N,N-dimethylformamide (75 mL) in a room temperature water bath under nitrogen. The water bath was removed, and to the dark solution was added copper powder (0.74 g), 4-chloro-3-nitrotoluene (10.0 g) and N,N-dimethylformamide (25 mL). The mixture was heated to 125° C. for 16 hours and evaporated under vacuum. The residue was partitioned between chloroform and water, and the layers were separated. The chloroform layer was washed with 1 N NaOH, water, and brine, dried over magnesium sulfate, and evaporated under vacuum. The crude oil was distilled under vacuum, and a fraction boiling at 148° C. (0.25 mm Hg) was collected to yield the title compound as a yellow oil.

(b) 5-methyl-2-phenoxybenzeneamine

A solution of the title compound of Example 17(a) (7.5 g) in methanol (30 mL) was shaken in a Parr Hydrogenator over 5% palladium on carbon at 5 psi hydrogen at room temperature for 18 hours. The catalyst was filtered from the reaction, and the solution was evaporated under vacuum to yield the title compound as a yellow oil.

(c) 8-methyldibenz[b,f][1,4]oxazepin-11(10H)-one

To a solution of phosgene (1.93 M in toluene, 65 mL) under nitrogen at approximately 5° C. was added dropwise a solution of 5-methyl-2-phenoxybenzeneamine (5.0 g) in toluene (15 mL). The resulting solution was stirred at 0°–5° C. for 30 minutes, and heated on a steam bath for 35 minutes under nitrogen. Evaporation under vacuum yielded the isocyanate compound as a clear oil. IR: 2250 cm (strong). The isocyanate compound was taken up in bromobenzene (30 mL) and added dropwise to a stirred mixture of aluminum chloride (3.35 g) in bromobenzene (30 mL) at 100° C. under nitrogen. The reaction temperature was raised to 150° C., and the reaction was stirred for one hour. The reaction was poured into ice/water (250 g) and extracted twice with chloroform. The combined chloroform extracts were washed with water, 1 N HCl, saturated sodium bicarbonate, and brine, dried over magnesium sulfate, and evaporated under vacuum. The residue was suspended in ether, and the insoluble product was collected by filtration and washed with ether to yield the title compound as white crystals. Mp: 231°–232° C.

(d) 10,11-dihydro-8-methyldibenz[b,f][1,4]oxazepine

A solution of lithium aluminum hydride (1.0 M in tetrahydrofuran, 60 mL) was added dropwise under nitrogen to a stirred solution of the title compound of Example 17(c) (4.5 g) in tetrahydrofuran (300 mL) in an ice water bath, keeping the temperature below 10° C. The ice water bath was removed, and the reaction was stirred at ambient temperature for 45 minutes. The reaction was then refluxed for 4.5 hours, and the resulting mixture was cooled to approximately 5° C. and quenched by the successive addition of water (2.3 mL), 15% NaOH (2.3 mL), and water (6.9 mL). The reaction was filtered, and the filtrate was evaporated under vacuum to a cloudy oil which solidified on standing. The solid was taken up in chloroform, and the solution was washed with 1 N NaOH, water, and brine, dried over magnesium sulfate, and evaporated under vacuum. Flash chromatography through silica gel 60 using chloroform yielded the title compound as a yellowish-white, waxy solid. Mp: 84°–86° C.

(e) 8-methyldibenz[b,f][1,4]oxazepine-10(11 H)-carboxylic acid, 2-[3-(ethylsulfonyl)-1-oxopropyl]hydrazide To a stirred solution of phosgene (1.93 M in toluene, 9.0 mL) in tetrahydrofuran (40 mL) at approximately 5° C. (ice water bath) under nitrogen was added dropwise a solution of the title compound of Example 17(d) (2.00 g) and triethylamine (1.4 mL) in tetrahydrofuran (40 mL). The ice bath was removed, and the reaction was stirred at ambient temperature for 2 hours. The reaction was evaporated under vacuum, and to the residue was added 2-[3-(ethylsulfonyl)-1-oxopropyl]hydrazide (1.71 g), triethylamine (1.4 mL), and toluene (50 mL). The reaction mixture was refluxed for 1.5 hours, and evaporated under vacuum. The residue was partitioned between chloroform and water, and the layers were separated, and the chloroform layer was washed with water, 1 N HCl, water, saturated sodium bicarbonate, and

EXAMPLE 18

4-chlorodibenz[b,f][1,4]oxazepine-10(11 H)-carboxylic acid, 2-[3-(ethylsulfonyl)-1-oxopropyl]hydrazide

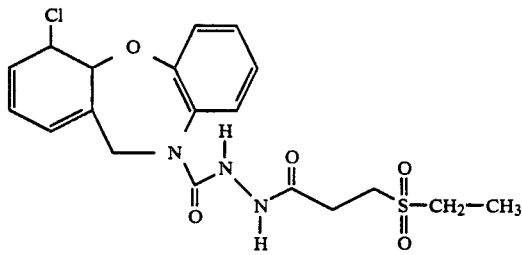

(a) 2-chloro-1-(2-nitrophenoxy)benzene

Sodium hydride (1.00 g) was added in portions to a solution of 2-chlorophenol (5.00 g) in N,N-dimethylformamide (100 mL) under nitrogen. To the resulting solution was added 2-fluoro-1-nitrobenzene (5.00 g). The mixture was heated at 65° C. overnight, and then was evaporated under vacuum. The residue was partitioned between chloroform and 1 N NaOH, and the layers were separated. The aqueous layer was extracted once more with chloroform, and the combined chloroform layers were washed with water and brine, dried over magnesium sulfate, and evaporated under vacuum to a yellow oil. The oil was crystallized from ethyl ether/hexane at −78° C. to yield the title compound as a light yellow solid. Mp: 48°–49° C.

(b) 2-(2-chlorophenoxy)benzeneamine

A solution of 2-chloro-(2-nitrophenoxy)benzene (5.00 g) in tetrahydrofuran (100 mL) was shaken in a Parr Hydrogenator over Raney nickel at 5 psi hydrogen at room temperature for 4 hours. The catalyst was filtered from the reaction, and the solution was evaporated under vacuum to a yellowish oil which crystallized on standing. The solid was crushed, suspended in hexane and filtered to yield the title compound as a light orange solid. Mp: 44°–45° C.

(c) 4-chlorodibenz[b,f][1,4]oxazepin-11(10H)-one

To a solution of phosgene (1.93 M in toluene, 42 mL) under nitrogen at approximately 5° C. was added dropwise a solution of the title compound of Example 18(b) (3.50 g) in toluene (11 mL). The mixture was stirred at 0°–5° C. for 30 minutes, and then heated on a steam bath for 30 minutes under nitrogen. Evaporation under vacuum yielded the isocyanate compound as a clear oil. IR: 2250 cm (strong). The isocyanate compound was taken up in bromobenzene (2; mL) and added dropwise to a stirred mixture of aluminum chloride (2.14 g) in bromobenzene (21 mL) at 100° C. under nitrogen. The reaction temperature was raised to 150° C., and the reaction was stirred for two hours. The reaction was evaporated under vacuum, and the residue was vigorously shaken with ethyl acetate/1 N NaOH. The resulting emulsion was filtered through a sintered glass funnel, and the resulting layers were separated. The semi-solid which had collected on the filter was washed with ethyl acetate, and this wash was combined with the ethyl acetate from the filtrate. The ethyl acetate layers were combined, washed with 1 N NaOH, 1 N HCl, and brine, dried over magnesium sulfate, and evaporated under vacuum to an oily, solid, yellow residue. This was triturated with ethyl ether, and the solid was collected by filtration. This solid was added to the semi-solid collected earlier, and the combined solids were washed with ether and air dried. The crude product was refluxed with ethanol (3A, 200 mL) for one hour, evaporated to dryness, triturated with ethyl ether, and the solid was collected. Drying under vacuum at 56° C. yielded the title compound as a white solid.

(d) 4-chloro-10,11-dihydrodibenz[b,f][1,4]oxazepine

A solution of lithium aluminum hydride (1.0 M in tetrahydrofuran, 60 mL) was added dropwise under nitrogen to a stirred solution of the title compound of Example 18(c) (3.00 g) in tetrahydrofuran (100 mL) in an ice water bath keeping the temperature below 15° C. The ice bath was removed, and the reaction was stirred at reflux for 3.5 hours, and the resulting mixture was cooled to approximately 5° C. and quenched by the successive addition of water (2.3 mL), 15% NaOH (2.3 mL), and water (6.9 mL). The reaction was filtered, and the solid was rinsed with tetrahydrofuran. The rinse and filtrate were combined and evaporated under vacuum. Flash chromatography through silica gel 60 using 4:1 hexane:ethyl acetate yielded the title compound as an oil which solidified on standing to a white solid. Mp: 71°–73° C.

(e) 4-chlorodibenz[b,f]1,4]oxazepine-10(11 H)-carboxylic acid, 2-[3-(ethylsulfonyl)-1-oxopropyl]hydrazide To a stirred solution of phosgene (1.93 M in toluene, 6.5 mL) in tetrahydrofuran (30 mL) at approximately 5° C. (ice water bath) under nitrogen was added dropwise a solution of the title compound of Example 18(d) (1.50 g) and triethylamine (1.0 mL) in tetrahydrofuran (20 mL). The ice bath was removed, and the reaction was stirred at ambient temperature for 2 hours. The reaction was evaporated under vacuum, and to the residue was added 2-[3-(ethylsulfonyl)-1-oxopropyl]hydrazide (1.28 g), triethylamine (1.0 mL), and toluene (35 mL). The reaction mixture was refluxed for 3 hours under nitrogen and evaporated under vacuum until most of the toluene had been removed. The residue was treated with ethyl ether, and the precipitated solid was collected by filtration. The solid was washed with ethyl ether, suspended in 1 N HCl (25 mL), and heated on a steam bath for 5 minutes. After cooling to 5° C., the insoluble crude product was collected by filtration, washed with ethyl ether, and crystallized from ethanol (3A) to yield the title compound as white crystals. Mp: 195°–197° C.

EXAMPLE 19

8-hydroxydibenz[b,f][1,4]oxazepine-10(11H)-carboxylic acid, 2-[3-(ethylsulfonyl)-1-oxopropyl]hydrazide

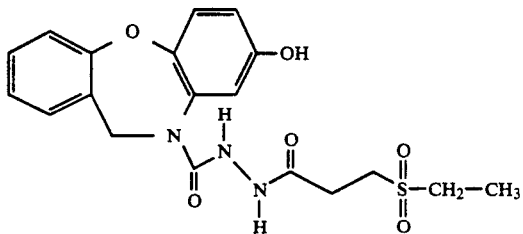

To a stirred solution of boron tribromide (1.0 M in methylene chloride, 7.2 mL) at 5° C. (ice water bath) was added under nitrogen the title compound of Example 16(e) (1.0 g). The ice bath was removed, and the reaction was stirred at room temperature for 3 hours. The reaction was carefully quenched by the addition of 1 N NaOH (10 mL), acidified by the addition of 1 N HCl (15 mL), and evaporated under vacuum. The resulting solid was triturated with water, and the insoluble material was collected by filtration, washed three times with water, and then with ethyl ether. Crystallization from ethanol (3A) yielded the title compound as white crystals. Mp: 191°-194° C.

EXAMPLE 20

8-(trifluoromethyl)dibenz[b,f][1,4]oxazepine-10(11H)-carboxylic acid, 2-[3-(ethylsulfonyl)-1-oxopropyl]hydrazide

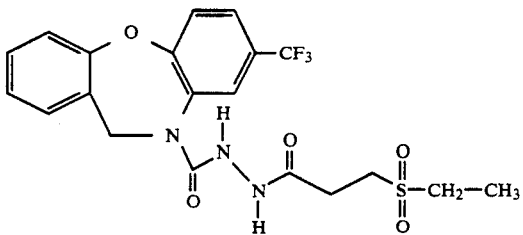

200 parts of 4-chloro-3-nitrobenzotrifluoride was heated to 160° C. and stirred and 160 parts of the potassium salt of salicylaldehyde was added over a period of 30 minutes. After the addition was complete, an exothermic reaction took place and the temperature rose to about 195° C. Heating was then discontinued until the reaction subsided, and the mixture was then heated for 1 hour at 150° C. The mixture was cooled, ice and water were added, and it was then extracted with ether. The ether layer was filtered to remove insoluble material, and the resultant solution was dried over sodium sulfate. The ether solvent was then evaporated and the residual oil was recrystallized from a mixture of hexane and benzene to give 2-(2-nitro-4-trifluoromethylphenoxy)-benzaldehyde melting at about 79°-81° C.

A solution of 55 parts of the ether obtained in the preceding paragraph in 800 parts of ethanol was hydrogenated over Raney nickel catalyst at room temperature and atmospheric pressure. When hydrogen uptake ceased, the catalyst was removed by filtration and the ethanol solvent was evaporated. The residue was then dissolved in 500 parts by volume of hexane, filtered, and then cooled. There was then obtained yellowish-white crystals which were separated by filtration to give 8-(trifluoromethyl)10,11,-dihydrodibenz -[b,f][1,4]oxazepine melting at about 86°-88° C.

To a stirred solution of phosgene (1.93 M in toluene, 5.4 mL) in tetrahydrofuran (23 mL) at approximately 5° C. (ice water bath) under nitrogen was added dropwise a solution of 8-(trifluoromethyl)-10,11-dihydrodibenz[b,f][1,4]oxazepine (1.50 g) and triethylamine (0.8 mL) in tetrahydrofuran (14 mL). The ice bath was removed, and the reaction was stirred at ambient temperature for 1 hour. The reaction was evaporated under vacuum, and to the residue was added 2-[3- ethylsulfonyl)-1-oxopropyl]hydrazide (1.03 g), triethylamine (0.8 mL) and toluene (28 mL). The reaction mixture was refluxed for 2 hours, and stirred at room temperature for 16 hours. The reaction was diluted with ether, and the precipitate was collected by filtration. After washing with ether, the precipitate was suspended in water, heated on a steam bath for 5 minutes, and cooled to room temperature. The insoluble product was collected by filtration, washed with water followed by ether, and crystallized from toluene to yield the desired title compound as a white powder. Mp: 139°-145° C.

EXAMPLE 21

Dibenz[b,f][1,4]oxazepine-10(11H)-carboxylic acid, 2-[3-(ethylsulfonyl)-1-oxopropyl]hydrazide

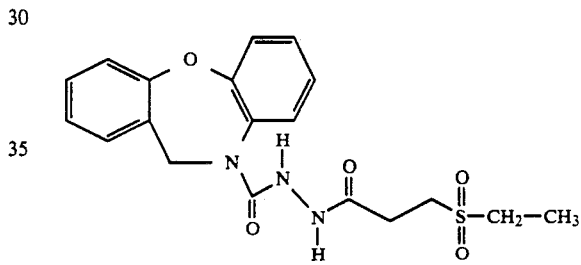

A solution of 2.0 g of 8-chloro-10,11-dihydrodibenz[b,f][1,4]oxazepine, 0.77 g of sodium hydroxide, and 5% palladium on carbon in 50 mL of ethanol (3A) was shaken at 60 psi hydrogen in a Parr hydrogenator at room temperature for 3.67 hours. The catalyst was filtered from the reaction and the solution was evaporated under vacuum. The residue was taken up in chloroform, washed with water and brine, dried over magnesium sulfate, and evaporated under vacuum to yield 1.16 g (68.1%) of 10,11-dihydrodibenz[b,f][1,4]oxazepine as a tan solid. Mp: 74°-76° C.

To a stirred solution of phosgene (1.93 M in toluene, 4.8 mL) in tetrahydrofuran (20 mL) at approximately 5° C. (ice water bath) under nitrogen was added dropwise a solution of 10,11-dihydrodibenz[b,f][1,4]oxazepine (1.0 g) and triethylamine (0.73 mL) in tetrahydrofuran (12 mL). The ice bath was removed, and the reaction was stirred at ambient temperature for 2 hours. The reaction was evaporated under vacuum, and to the residue was added 2-[3-(ethylsulfonyl)-1-oxopropyl]hydrazide (0.914 g), triethylamine (1.6 mL), and toluene (25 mL). The reaction mixture was refluxed for 2 hours and evaporated under vacuum. The residue was partitioned between chloroform and water, the layers were separated, and the chloroform layer was washed with water and brine, dried over magnesium sulfate, and evaporated under vacuum. The crude product was flash chromatographed through silica gel 60 using chloroform. Crystallization of the chromatographed product yielded the pure product as a white solid. Mp: 173°–177° C.

EXAMPLE 22

8-chloro-10,11-dihydrodibenzo[b,f][1,4]thiazeoine-10-(11 H) carboxylic acid, 2-[3-(ethylsulfonyl)-1-oxopropyl]hydrazide

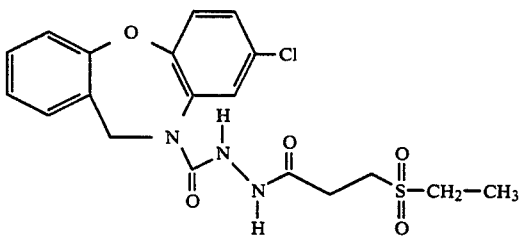

(a) 4-chloro-2-nitro-1-(phenylthio)benzene

Potassium hydroxide (6.15 g; 87%) was added to a stirred solution of thiophenol (10.0 g) in N,N-dimethylformamide (170 mL) at room temperature. When most of the potassium hydroxide appeared to have dissolved, 2,5-dichloronitrobenzene (17.4 g) was added, and the initially dark solution turned a bright yellow with some precipitate. The reaction was placed in an oil bath at 70° C. for three hours, and then evaporated in vacuo. The residue was partitioned between chloroform and 1 N NaOH and the layers were separated. The aqueous layer was extracted once more with chloroform. The chloroform solutions were combined, washed with 1 N NaOH, $H_2O$, 1 N HCl, $H_2O$ and brine, dried over $MgSO_4$, and evaporated in vacuo. The resulting oil was treated with cyclohexane, and the product crystallized. The crystalline product was collected by filtration, washed with hexane, and dried in vacuo at 56° C. to yield 13.73 g (57%) of yellow crystals. mp: 84°–86° C.

(b) 5-chloro-2(phenylthio)benzenamine

A solution of 4-chloro-2-nitro-1-(phenylthio)benzene (11.0 g) and Raney nickel in ethanol (3A; 9.3 mL) was reacted in a Parr Hydrogenator under hydrogen atmosphere at 5 psi and room temperature. When the theoretical amount of hydrogen uptake was reached, the reaction was filtered to remove the catalyst and evaporated in vacuo to yield 8.61 g (88%) of a light orange solid. mp: 59°–61° C.

(c) 8-chloro-10,11-dihydrodibenzo[b,f][1,4]thiazepine

To a cold (ice water bath), stirred solution of phosgene (1.93 M in toluene; 55 mL) under a nitrogen atmosphere was added, dropwise, a solution of 5-chloro-2-(phenylthio)benzenamine (5.00 g) in toluene (20 mL). The reaction mixture was stirred for 30 minutes in the ice bath, and was then heated on a steam bath for 30 minutes. The resulting orange solution was evaporated in vacuo to an oil (IR: weak band at approximately 2250 cm$^{-1}$).

The oil was taken up in bromobenzene 25 mL) and added dropwise to a stirred mixture of aluminum chloride (2.90 g) in bromobenzene (25 mL) in an oil bath at 100° C. When the addition was complete, the oil bath temperature was increased to 150° C., and the reaction was stirred for 1.5 hours. A small amount of water was then added to quench the reaction, and the mixture was evaporated in vacuo. The residue was triturated with acetone, and the solid was collected by filtration, washed with acetone followed by ether, and dried in vacuo at 110° C. for 16 hours to yield 6.99 of white solid.

The white solid (6.64 g) was suspended with stirring in anhydrous tetrahydrofuran (175 mL) under a nitrogen atmosphere in an ice-$H_2O$ bath, and lithium aluminum hydride (1.0 M in THF; 100 mL) was added dropwise, keeping the temperature below 10° C. When the addition was complete, the ice bath was removed and the reaction stirred to room temperature (approximately 20 minutes), and then at reflux for four hours under a nitrogen atmosphere. The reaction was then cooled in an ice-$H_2O$ bath and quenched by the successive addition of $H_2O$ (3.8 mL), 15% NaOH (3.8 mL), and $H_2O$ (11.4 mL) while keeping the temperature below 15° C. The resulting mixture was filtered through filter aide and the filter cake was washed with THF. The filtrate and washes were combined and evaporated in vacuo to a yellow oil. The oil was flash chromatographed through silica gel 60 (approximately 300 mL) using chloroform. The collected product was recrystallized from cyclohexane to yield 2.37 g (42.7%) of product as white plates. mp: 125°–127° C.

(d) 8-chloro-10,11-dihydrodibenzo[b,f][1,4]-thiazeoine -10(11 H)-carboxylic acid, 2-[3-(ethylsulfonyl) -1-oxopropyl]-hydrazide To a cold (ice-$H_2O$ bath), stirred solution of phosgene (1.93 M in toluene; 8.6 mL) in anhydrous tetrahydrofuran (40 mL) under a nitrogen atmosphere was added, dropwise, a solution of 8-chloro-10,11-dihydrodibenzo[b,f][1,4]-thiazepine (2.00 g) and triethylamine (1.3 mL) in anhydrous tetrahydrofuran (30 mL). The resulting mixture was stirred at room temperature for 90 minutes, and the solvent was then evaporated in vacuo. To the residue was added toluene (50 mL), 2-[3-(ethylsulfonyl)-1-oxopropyl]hydrazide (1.53 g), and triethylamine (1.3 mL), and the reaction was stirred at reflux under a nitrogen atmosphere for 3.5 hours, and then at room temperature overnight. The reaction was diluted with ethyl ether (100 mL) and the undissolved material collected by filtration. The collected material was washed with ether, suspended in $H_2O$ (50 mL), and heated on a steam bath for 5 minutes. The undissolved material was again collected by filtration and was washed with $H_2O$ followed by ether. After air drying for one hour, the crude product was flash chromatographed through silica gel 60 (approximately 350 mL) using 3:1 chloroform:tetrahydrofuran. This product was chromatographed a second time via medium pressure chromatography through silica gel 60 using 95:5 chloroform:methanol. The collected product was dried in vacuo at 56° C. for 48 hours to yield 2.20 g (60.0%) of the desired title compound of Example 22 as a solidified foam.

Analysis calculated for $C_{19}H_{20}ClO_4S_2$: C, 49.24; H, 4.35; N, 9.02; Cl, 9.89; S, 13.76. Found: C, 48.84; H, 4.29; N, 9.03; Cl, 9.64; S, 13.96. HPLC: 100%.

EXAMPLE 23

8-chloro-10,11-dihydrodibenzo[b,f][1,4]thiazepine-10 (11 H) carboxylic acid, 2-[3-(ethylsulfonyl)-1-oxopropyl]hydrazide, 5,5-dioxide

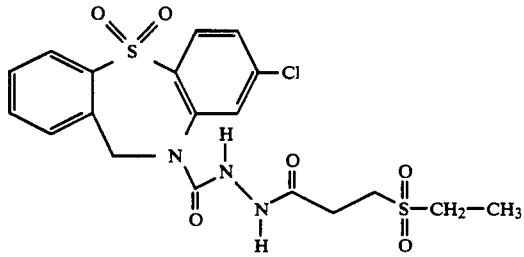

To a cold (ice-H$_2$O bath), stirred solution of the title compound of Example 22 )0.75 g) in methylene chloride (15 mL) was added a solution of m-chloroperoxybenzoic acid (55%; 1.05 g) in methylene chloride (15 mL). The solution was stirred in the ice bath for 3.5 hours, diluted with chloroform, and washed with saturated NaHSO$_3$ (2×200 mL), saturated NaHCO$_3$ (2×200 mL), and brine (200 mL). The solution was dried over MgSO$_4$ and evaporated in vacuo. The crude product was flash chromatographed through silica gel 60 (approximately 300 mL) using 1:1 chloroform:tetrahydrofuran. The purified product was taken up in ethanol (3A) and evaporated in vacuo to yield a white solid. Recrystallization from ethanol (3A) yielded 303 mg (37.7%) of the desired title compound as white crystals.

Analysis calculated for C$_{19}$H$_{20}$ClO$_6$S$_2$: C, 46.96; H, 4.15; N, 8.65; Cl, 7.30; S, 13 20. Found: C, 46.87; H, 4.22; N, 8.61; Cl, 7.31; S, 13.06. HPLC: 99.06%. DSC: 218°–219° C.

The identity and purity of the products synthesized in the examples presented above were confirmed by $^1$H NMR, $^{13}$C NMR, microanalysis, and high performance liquid chromatography (HPLC). The results of these analyses are presented in Table 1 below.

tion. These examples are merely illustrative, however, and should not be read as limiting the scope of the invention as it is claimed in the appended claims.

(7) The Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., Arch. int. Pharmacodyn, 267, 131–140 (1984); C. Vander Wende et al., Fed. Proc., 15, 494 (1956); Koster et al., Fed. Proc., 18, 412 (1959); and Witken et al., J. Pharmacol. exp. Ther., 133, 400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table 2 below.

Charles River male albino mice, weighing 20 to 30 grams were used in this assay.

Twenty-five minutes after subcutaneous or intragastric administration to ten mice of 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the num-

TABLE 1

Analytical Data — Elemental Analysis

| Example Number | % C Calc. | % C Found | % H Calc. | % H Found | % N Calc. | % N Found | % Cl Calc. | % Cl Found | % S Calc. | % S Found | HPLC (%) | Mp (°C.) |
|---|---|---|---|---|---|---|---|---|---|---|---|---|
| 5 | 56.23 | 56.04 | 5.90 | 5.97 | 8.19 | 7.77 | —* | — | — | — | 97.64 | 130–142 |
| 3(d) | 57.24 | 57.58 | 5.80 | 5.99 | 8.34 | 7.74 | — | — | — | — | 99.66 | — |
| 2 | 54.66 | 54.75 | 5.02 | 5.09 | 9.10 | 9.01 | — | — | 6.95 | 6.80 | 99.09 | 211–212 |
| 1(e) | 54.66 | 1.09 | 5.02 | 5.04 | 9.11 | 9.03 | — | — | 6.95 | 7.07 | 100.0 | 172–176 |
| 7(c) | 54.14 | 53.76 | 4.78 | 4.79 | 9.97 | 9.85 | — | — | — | — | 99.80 | 191–193 |
| 8(c) | 56.56 | 55.78 | 5.25 | 5.32 | 10.42 | 10.13 | — | — | — | — | 99.90 | 184–185 |
| 9(c) | 48.31 | 48.25 | 4.05 | 4.01 | 8.90 | 8.95 | — | — | — | — | 99.93 | 189–190 |
| 6 | 53.69 | 53.47 | 4.73 | 4.92 | 9.39 | 9.05 | — | — | — | — | 100.0 | 185–191 |
| 4 | 53.68 | 53.48 | 4.73 | 4.72 | 9.39 | 9.31 | — | — | — | — | 98.97 | 191–194 |
| 10(d) | 50.89 | 50.79 | 4.50 | 4.52 | 12.49 | 12.50 | — | — | 7.15 | 7.10 | 99.95 | 198–200 |
| 11(d) | 56.07 | 56.04 | 4.70 | 4.80 | 13.08 | 13.19 | — | — | — | — | 99.91 | 188–190 |
| 12(d) | 52.12 | 51.74 | 4.60 | 4.65 | 9.60 | 9.32 | — | — | — | — | 100.0 | 209–211 |
| 13 | 54.54 | 54.48 | 5.30 | 5.38 | 13.39 | 13.31 | — | — | 7.66 | 7.63 | 99.14 | 172–179 |
| 14 | 48.38 | 48.44 | 4.87 | 4.85 | 11.28 | 11.53 | — | — | 12.91 | 12.75 | 100.0 | 211–212 |
| 15 | 57.12 | 57.28 | 6.46 | 6.41 | 11.59 | 11.52 | — | — | — | — | 99.53 | — |
| 16(e) | 55.42 | 55.30 | 5.35 | 5.40 | 9.69 | 9.62 | — | — | — | — | 99.03 | 187–190 |
| 17(e) | 57.54 | 57.49 | 5.55 | 5.51 | 10.06 | 10.00 | — | — | — | — | 99.81 | 167–169 |
| 18(e) | 52.12 | 52.21 | 4.60 | 4.61 | 9.60 | 9.58 | 8.10 | 8.14 | 7.32 | 7.38 | 100.0 | 195–197 |
| 19 | 54.41 | 54.51 | 5.05 | 5.06 | 10.02 | 10.06 | — | — | 7.64 | 7.39 | 99.50 | 191–194 |
| 20 | 50.95 | 50.65 | 4.28 | 4.18 | 8.91 | 8.79 | — | — | 6.80 | 6.98 | 99.70 | 139–145 |
| 21 | 56.56 | 55.78 | 5.25 | 5.32 | 10.42 | 10.13 | — | — | 7.95 | 7.74 | 98.86 | 173–177 |

*Indicates that chlorine and sulfur were not present in the compound and, thus, that no analyses were performed for these elements.

The foregoing examples are provided to enable one of ordinary skill in the art to practice the present invenber of writhes occurring during the following ten-minute period was counted.

A test compound was considered to have produced analgesia in a mouse if, in accordance with the conditions set forth above, and under the test criteria employed for this assay, after the administration of 30 mg per kilogram of body weight of a compound of the present invention to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," *Advances in Biochemical Psychopharmacology*, 8, 191 1974).

The results for the particular compounds of the present invention analyzed in this assay, and discussed in the examples identified below which correspond thereto, are presented in Table 2 hereinbelow under the heading "WRITHING ASSAY." The fractions indicate the number of mice out of ten in which a test compound produced analgesia. 8-(trifluoromethyl)dibenz[b,f][1,4]oxazepine-10(11 H)-carboxylic acid, 2-[3-(ethylsulfonyl)-1-oxopropyl]hydrazide (Example 20) was determined to be the most potent compound of the invention tested in this assay, and is the most preferred compound of the present invention.

(b) Prostaglandin (PGE) Antagonism Assay

In order to determine the effectiveness of several of the compounds of the present invention ("test compounds") as prostaglandin $E_2$ antagonists, a prostaglandin antagonism assay was conducted, as described below, to determine the ability of these compounds to inhibit prostaglandin $E_2$-induced contractions of segments of guinea pig ileum. If a test compound inhibits prostaglandin $E_2$-induced contractions, it suggests that the compound functionally antagonizes prostaglandin $E_2$.

Male albino guinea pigs weighing 200 to 500 grams were sacrificed by cervical dislocation. The ilea were then quickly removed from the guinea pigs and placed in a modified Tyrode solution, a solution which is known to those skilled in the art, containing one-half of the usual amount of magnesium ions.

Segments of ileum about 2 cm long were then cut and mounted in a 10-mL tissue bath containing the modified Tyrode solution. The solution was maintained at 37° C. and aerated with a gaseous mixture of 95% oxygen and 5% carbon dioxide. Data for a control prostaglandin $E_2$ dose response curve plotting concentration of prostaglandin $E_2$ versus the intensity of contractions, detected isotonically, was then obtained by experimentally adjusting the dose of the prostaglandin $E_2$ being injected into the tissue bath, in a manner known by those of skill in the art.

Solutions or suspensions containing an initial concentration (3 micromolar) of a test compound in modified Tyrode solution ("test solutions/suspensions") were then separately substituted for the control bath solution. Each test solution/suspension was then kept in constant contact with the ileum tissue, except for brief periods to drain the bath in preparation for rinsing with fresh test solution/suspension. A second prostaglandin $E_2$ dose response curve was then generated for prostaglandin $E_2$ in the presence of a test compound.

A dose ratio of $EC_{50}$ doses was then calculated from the results of each test in a manner known by those of skill in the art. A test compound was determined to be "active" if the initial concentration used yielded at least a two-fold shift (dose ratio greater than or equal to 2) in the dose response curve for prostaglandin $E_2$. An estimated $pA_2$ value (a statistical constant which is a common measure of expressing the potency of a particular drug as an antagonist) was reported for "active" compounds under the assumption that the slope of the Schild plot does not deviate significantly from $-1.0$. If the initial concentration of test compound yielded at least a five-fold shift (dose ratio greater than or equal to 5) in the dose response curve for prostaglandin $E_2$, then varying concentrations of the test compound were assayed, and a $pA_2$ value for that compound was calculated by Schild plot calculations, as described by H.O. Schild, "pA, A New Scale for the Measurement of Drug Antagonism," Br. J. pharmacol, 2, 189 (1947). The higher the value calculated for the $pA_2$, the more potent a particular compound is as a prostaglandin $E_2$ antagonist.

The results of this prostaglandin antagonism assay are also presented in Table 2 below. The compounds of the present invention which were tested in this assay, and for which results are presented in Table 2, correspond to the particular examples specified in Table 2.

TABLE 2

| | Data Generated from the Assays | | |
|---|---|---|---|
| Example Number | WRITHING ASSAY Number Out of Ten | | PGE ANTAGONISM IN GUINEA PIG ILEUM ($pA_2$) |
| | S.C. | I.G. | |
| 5 | 3/10 | 2/10 | 5.93 |
| 3 | 3/10 | 4/10 | 5.75 |
| 2 | 3/10 | 3/9 | 5.70 |
| 1 | 5/10 | 3/10 | 5.54 |
| 7 | 6/10 | 4/10 | * |
| 8 | 6/10 | 6/10 | * |
| 9 | 3/10 | 4/10 | 5.8 |
| 6 | 2/10 | 4/10 | 5.58 |
| 4 | 4/10 | 3/10 | * |
| 10 | 4/10 | 4/10 | 5.54 |
| 11 | 5/10 | 5/9 | * |
| 12 | 4/10 | 3/10 | 5.94 |
| 13 | 4/10 | 4/10 | 5.55 |
| 14 | 6/10 | 6/10 | * |
| 15 | 1/10 | 3/10 | 6.15 |
| 16 | 2/10 | 6/10 | 5.70 |
| 17 | 2/10 | 2/9 | 5.68 |
| 18 | 4/10 | 4/10 | 5.57 |
| 19 | 3/10 | 4/10 | 5.59 |
| 20 | 6/10 | 6/10 | 5.9 |
| 21 | 1/10 | 5/10 | 5.98 |
| 22 | 3/10 | 6/10 | ** |
| 23 | 7/10 | 3/10 | ** |

*Indicates that, in accordance with the particular conditions set forth above in the Prostaglandin Antagonism Assay, and under the test criteria employed for that assay, after the administration of an initial screening dosage of 3 micromolar of the compound, a two-fold shift in the dose response curve for prostaglandin $E_2$ was not yielded.
**Not tested.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A compound of having the structure:

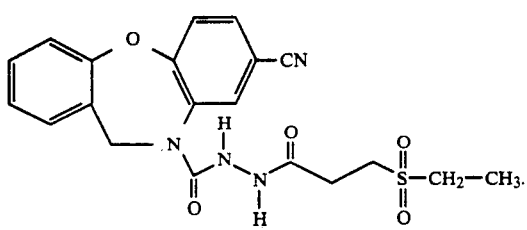

2. A compound having the structure:

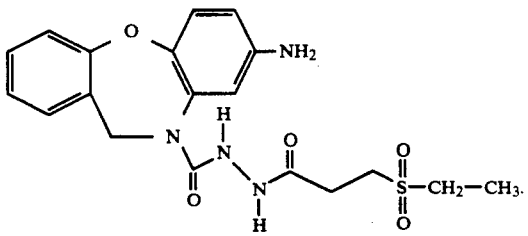

3. A compound having the structure:

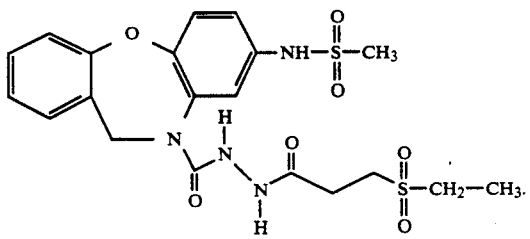

* * * * *